(12) United States Patent
Troxler

(10) Patent No.: US 12,146,842 B2
(45) Date of Patent: Nov. 19, 2024

(54) PAVEMENT MATERIAL MICROWAVE DENSITY MEASUREMENT METHODS AND APPARATUSES

(71) Applicant: Troxler Electronic Laboratories, Inc., Research Triangle Park, NC (US)

(72) Inventor: Robert Ernest Troxler, Raleigh, NC (US)

(73) Assignee: Troxler Electronic Laboratories Inc, RTP, NC (US)

( * ) Notice: Subject to any disclaimer, the term of this patent is extended or adjusted under 35 U.S.C. 154(b) by 0 days.

(21) Appl. No.: 18/239,669

(22) Filed: Aug. 29, 2023

(65) Prior Publication Data

US 2023/0400419 A1 Dec. 14, 2023

Related U.S. Application Data

(63) Continuation of application No. 17/159,647, filed on Jan. 27, 2021, now Pat. No. 11,740,187, which is a continuation of application No. 14/500,969, filed on Sep. 29, 2014, now Pat. No. 10,908,096, which is a continuation of application No. 13/846,181, filed on Mar. 18, 2013, now Pat. No. 8,847,609, which is a continuation of application No. 11/712,060, filed on Feb. 28, 2007, now Pat. No. 8,400,168, which is a
(Continued)

(51) Int. Cl.
*G01N 22/00* (2006.01)
*G01N 22/04* (2006.01)
*G01N 33/38* (2006.01)
*G01N 33/42* (2006.01)

(52) U.S. Cl.
CPC .............. *G01N 22/00* (2013.01); *G01N 22/04* (2013.01); *G01N 33/38* (2013.01); *G01N 33/42* (2013.01)

(58) Field of Classification Search
CPC ........ G01N 22/00; G01N 22/04; G01R 27/26; G01R 27/2617
See application file for complete search history.

(56) References Cited

U.S. PATENT DOCUMENTS 5,369,369 A 11/1994 Cutmore
5,384,715 A 1/1995 Lytton
(Continued)

*Primary Examiner* — Lee E Rodak
*Assistant Examiner* — Demetrius R Pretlow
(74) *Attorney, Agent, or Firm* — NK Patent Law PLLC

(57) ABSTRACT

Portable microwave material gauge for determining the quality of a pavement material is provided. The gauge includes an electromagnetic field generator configured to generate an electric field mode that penetrates into the material wherein the material includes a heterogeneous material including at least one of a pavement material and a soil material, a calibration data set, a sensor of size and shape to support the electric field mode and to determine the response of the pavement material to the electric field wherein determining the response includes determining a change in the permittivity as a function of a change in the quality of the material; and an analyzer configured to correlate the sensor permittivity response to the calibration data set wherein correlating the response includes using stored relationships between the material quality and the sensor response using calibration samples having changes in permittivity as a function of quality.

24 Claims, 12 Drawing Sheets

Related U.S. Application Data continuation of application No. 10/971,546, filed on Oct. 22, 2004, now Pat. No. 7,239,150.

(60) Provisional application No. 60/514,031, filed on Oct. 24, 2003.

(56) References Cited

U.S. PATENT DOCUMENTS

| | | | |
|---|---|---|---|
| 5,420,589 A * | 5/1995 | Wells | G01V 3/12 342/22 |
| 5,588,032 A * | 12/1996 | Johnson | G01S 15/895 378/90 |
| 5,900,736 A | 5/1999 | Sovik et al. | |
| 5,939,889 A * | 8/1999 | Zoughi | G01N 33/28 324/643 |
| 5,952,561 A * | 9/1999 | Jaselskis | G01N 33/42 73/78 |
| 6,190,917 B1 * | 2/2001 | Barclay | G01N 5/04 219/757 |
| 6,204,670 B1 * | 3/2001 | Joshi | G01N 27/221 324/636 |
| 6,215,317 B1 | 4/2001 | Siddiqui et al. | |
| 6,414,066 B1 | 7/2002 | Lem et al. | |
| 6,577,141 B2 | 6/2003 | Gandrud | |
| 6,617,861 B1 | 9/2003 | Joshi | |
| 6,803,771 B2 | 10/2004 | Sovik et al. | |
| 7,219,024 B2 | 5/2007 | Gamache et al. | |
| 7,239,150 B2 | 7/2007 | Troxler et al. | |
| 7,569,810 B1 | 8/2009 | Troxler et al. | |
| 2001/0008773 A1 * | 7/2001 | Barclay | G01N 31/12 436/139 |
| 2002/0057095 A1 * | 5/2002 | Zoughi | G01N 33/383 324/646 |
| 2002/0157484 A1 * | 10/2002 | Bishara | G01N 33/42 374/45 |
| 2002/0180460 A1 * | 12/2002 | Geisel | G01N 22/00 324/640 |
| 2004/0260504 A1 | 12/2004 | Bienvenu et al. | |
| 2005/0252285 A1 | 11/2005 | Boehm | |
| 2007/0046289 A1 | 3/2007 | Troxler | |

\* cited by examiner

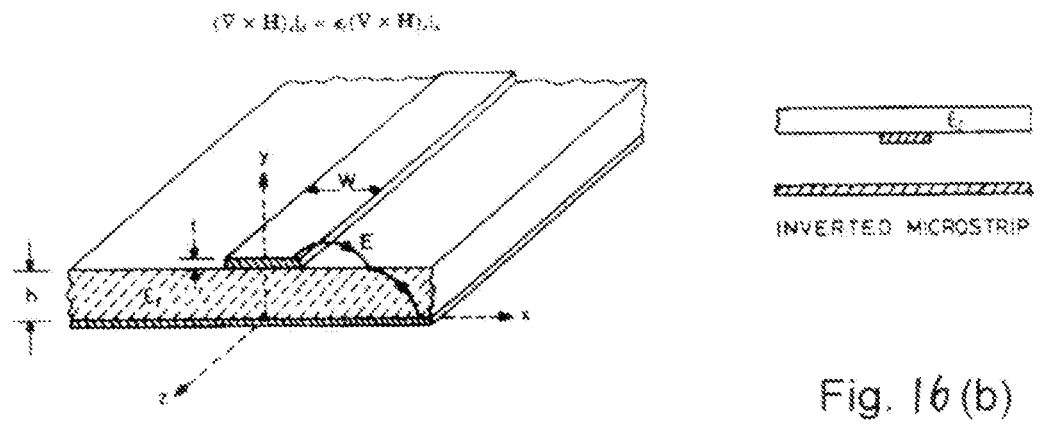
Fig. 16(a)
Fig. 16(b)
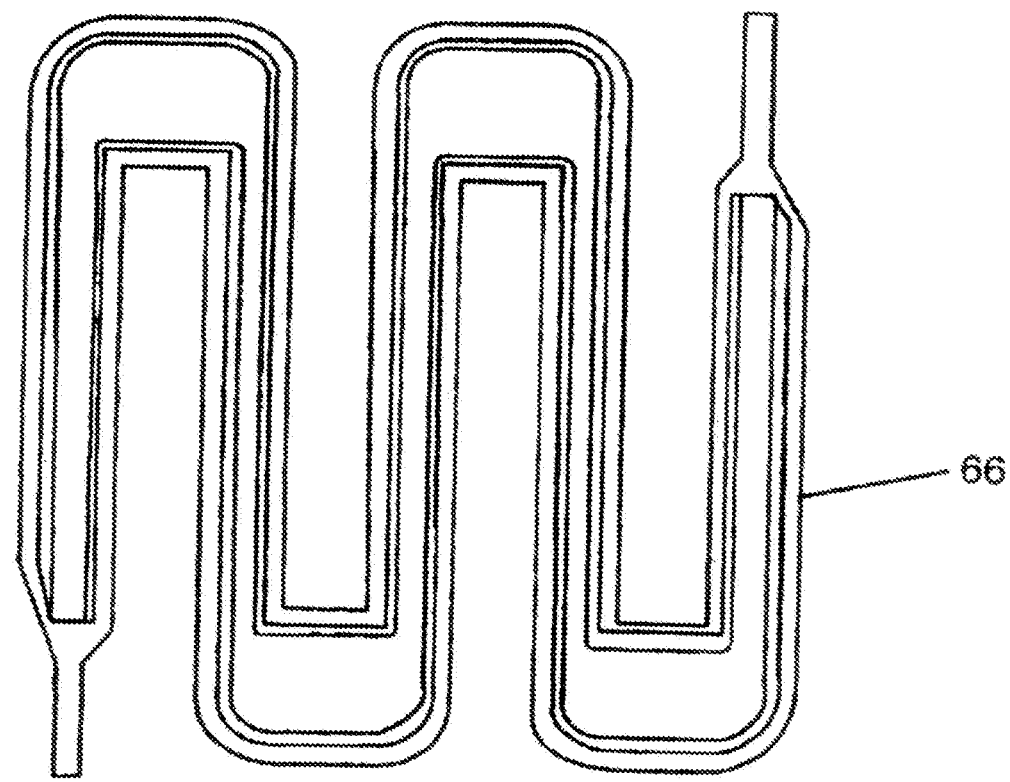
Fig. 17

PAVEMENT MATERIAL MICROWAVE DENSITY MEASUREMENT METHODS AND APPARATUSES

RELATED APPLICATIONS

This application is a continuation application of U.S. patent application Ser. No. 17/159,647, filed on Jan. 27, 2021, being issued as U.S. Pat. No. 11,740,187 on Aug. 29, 2023, which is a continuation of U.S. patent application Ser. No. 14/500,969, filed on Sep. 29, 2014, now U.S. Pat. No. 10,908,096 issued on Feb. 2, 2021, which is a continuation application of U.S. patent application Ser. No. 13/846,181, filed on Mar. 18, 2013, now U.S. Pat. No. 8,847,609 issued on Sep. 30, 2014, which is a continuation application of U.S. patent application Ser. No. 11/712,060, filed on Feb. 28, 2007, now U.S. Pat. No. 8,400,168 issued on Mar. 19, 2013, which is a continuation of U.S. patent application Ser. No. 10/971,546, filed Oct. 22, 2004, now U.S. Pat. No. 7,239,150 issued on Jul. 3, 2007, which claims the benefit of U.S. Provisional Patent Application Ser. No. 60/514,031, filed Oct. 24, 2003; the disclosure of all of which is incorporated herein by reference in its entirety.

TECHNICAL FIELD

This invention relates to the measurement of the quality of a pavement material such as soil, sand, aggregate, asphalt, and cement, and more particularly to a test instrument and method for measuring or correlating the density of a pavement sample using microwave bandwidths. The method is based on precise measurements of the real and imaginary parts of the permittivity in the frequency or time domain. It also has applications for measuring the free water content of construction materials.

BACKGROUND

Pavement materials, such as soil, sand, aggregate, asphalt, and cement, require quality testing for qualities such as moisture and density. Destructive tests and nondestructive tests are used throughout the industry for determining these qualities. In laboratory destructive tests, cylindrical samples are prepared, typically with a gyratory compactor, and various material properties are studied to determine the best mix design for a pavement. In field destructive tests, cylindrical samples are cored from test strips, newly constructed roads, or existing roads. The material properties of these samples are then used to evaluate whether the test strip or the new pavement meets the design criteria and whether the existing road is in good operating condition or in need of repairs.

Currently, several methods are used for measuring the density of cylindrical samples: dimensional analysis, the water displacement method, the paraffin coated method, and the para-film-covered method. In each case, the bulk density of a sample is derived by, as in the definition, dividing the dry sample mass by the estimated sample volume. All methods require a balance with a sensitivity of 0.1 g. to measure the mass of the sample. In the dimensional analysis method, sample volume is determined from the radius and thickness (height) measurements. Here, many readings of the radius and thickness of the sample are made using either manually vernier caliper or automatically using a laser system. The average values of the radius and the thickness are then used to calculate the sample volume.

Other methods use the Archimedes Principle for determining the sample volume. These methods require a large container filled with clean water. The water temperature should be monitored and controlled at a specific temperature, e.g. at 25° C. At one stage of the test, the sample is kept immersed in water for approximately 4 minutes and the weight of the sample, while suspended in water, is recorded. In the "paraffin-coated" method, after determining the dry weight of the sample, a thin coating of paraffin is applied to cover the entire surface area of the sample. Then, the sample is weighed again in air. Finally, the sample is weighed while immersed in water. More details can be found in standards ASTM D 2726 for the water displacement method and ASTM D 1188 for the paraffin-coated method.

Nondestructive field measurements of asphalt are typically accomplished with nuclear gauges. Nuclear radiation gauges have been widely used for measuring the density of soil and asphaltic materials. Such gauges typically include a source of gamma radiation which directs gamma radiation into the test material, and a radiation detector located adjacent to the surface of the test material for detecting radiation scattered back to the surface. From this detector reading, a determination of the density of the material can be made.

Nuclear gauges, however, require a high degree of training and radiological management for the operators of these gauges. Therefore, it would be desirable to obtain accurate field measurement gauges without the use of nuclear gauges.

SUMMARY

Methods and apparatuses for obtaining the density of a pavement material sample by microwave electromagnetic analysis are therefore provided. According to one embodiment of the invention, a method of obtaining a material property of a pavement material from a microwave field generally includes generating a microwave frequency electromagnetic field of a first mode about the pavement material. The frequency response of the pavement material in the electromagnetic field can be measured, such as by a network analyzer. One example of measuring frequency response may include obtaining scattering parameters for the frequency response although other frequency response parameters may be employed. The measurement of the frequency response permits correlating the frequency response to a material property of the pavement material sample, such as the density. Generally, the permittivity of a material permits direct correlation to the density of a material, and permittivity is a convenient way to assess density. However, the frequency response may be used to directly or indirectly calculate the density by other methods.

In further more particular embodiments of the invention, a method may also include calibration techniques. Calibration may be accomplished by generating a microwave frequency electromagnetic field of a first mode about a calibration material. The calibration material should have known physical properties such as density, volume, specific gravity, or porosity. Similar to the measurement method, a frequency response of the calibration material may be determined. The frequency response of the calibration material may be correlated to the known physical properties of the calibration material, thus providing calibration curve for the frequency response of the pavement material.

A method of correcting for the roughness of a pavement material is also provided. Generally the roughness may permit dividing the pavement into a shallow layer, the rough part, and a deep layer. Accordingly, a method of determining the permittivity of a pavement material having a shallow layer and a deep layer generally includes measuring a pavement material with first and second planar circuit permittivity sensors. The first planar circuit sensor measures the permittivity in a sample volume corresponding to at least a portion of both the shallow layer and the deep layer, the second planar circuit sensor measures permittivity in a sample volume corresponding at least a portion of the shallow layer. A calibration data set may be obtained for the first and second planar circuit sensors by calibrating to a plurality of known pavement material permittivities. The first planar circuit sensor measures the permittivity over the pavement material to permit determining a first measured permittivity. The second planar circuit sensor over the pavement material to permit determining a second measured permittivity. The first permittivity and second permittivity are correlated with the calibration data to determine the permittivity of the pavement material.

Additionally, embodiments of the invention include an apparatus for obtaining the density of a pavement sample. The apparatus generally includes a microwave circuit of a size and shape to generate an electromagnetic field about a pavement material. A network analyzer is interconnected to the microwave circuit to generate a microwave input to the circuit for generating the electromagnetic field. The network analyzer should be capable of measuring at least one scattering parameter. From the measured scattering parameter, the apparatus may determine the density of the pavement material.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIGS. 16(a) and (b) are microstrip microwave elements for obtaining the density of a pave material according to one embodiment of the invention.

FIG. 17 is a microstrip microwave element for obtaining the density of a pavement material according to one embodiment of the invention.

DETAILED DESCRIPTION

Figure 1:
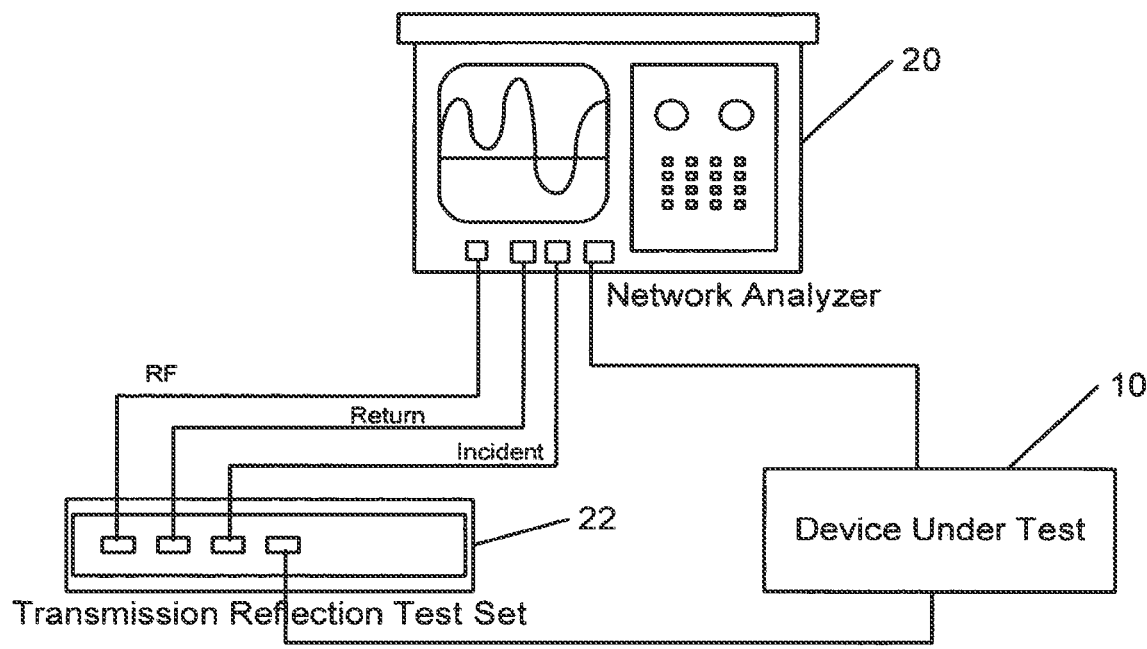
FIG. 1 is an apparatus for obtaining the density of a pavement material according to one embodiment of the invention.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Pavement materials, asphalt in particular, are heterogeneous mixtures of air, rocks, and binder. Each of these materials has a particular permittivity (i.e. the dielectric constant) associated with its ability to be polarized by an electric field. The permittivity is linearly related to the polarizability and is a complex quantity. The permittivity is generally complex having real, $\epsilon'$, and imaginary components, $\epsilon''$, representing energy storage and energy loss respectively to a propagating electromagnetic wave. Typically, when speaking of the dielectric constant one is referring to the real part of the permittivity.

Air has a dielectric constant of 1.0, asphalt binders have dielectric constant between 2.0 and 4.0, and rocks have dielectric constants that vary, but granite is about 4.0. In a moisture measuring mode, the microwave device would be used to measure the volume or mass percent of free water. Free water has a dielectric constant of 80 or less depending on the temperature. Bound water has a dielectric constant near that of ice of about 3 or 4. For a complicated heterogeneous mixture of materials like soil and water, the permittivity can be a strong function of frequency when measured swept over a 1 Ghz bandwidth. For HMA (hot mix asphalt), the aggregate is dried, and any residing water is bound to the aggregate. Bound moisture has a dielectric constant near 3 or 4. This is close to the permittivity of the binder and dry aggregates, and is not problematic as long as the mix remains consistent.

The measured permittivity of a material depends on the frequency and the type of charge carrier that is being displaced by an applied electric field. These charge carriers are displaced thus forming a net dipole moment. The charges can be electronic, atomic, polar and ionic. In asphalt, all of the above mechanisms contribute to the apparent dielectric constant. However, the main contributions are due to the polar and ionic responses, on a per unit volume basis. Additional solvents or impurities such as water will increase these contributions and the apparent dielectric constant. For low frequencies, the heavy ions respond and the Maxwell-Wagner effect makes the asphalt appear strongly polar and temperature dependent. At microwave frequencies, this effect is nonexistent. The Maxwell-Wagner effect also allows for the quantification of soil moisture and density of the heterogeneous materials.

The behavior of polar molecules in the asphalt follows a frequency-temperature response that can be modeled with a modified Debye equation. The dispersion in the microwave region is significantly decreased as a result of the reduction of the relaxation frequency. This reduction is anticipated due to the heavy asphalt molecules, and because of the asphalt bonding to the aggregate, which is of course the purpose of adding the binder in the first place.

Although the asphalt liquid is characterized as non-magnetic, the aggregates that make up the pavement mix could very well have a magnetic moment leading to a complex permeability $\mu'-j\mu''$. Here, g is the real part representing the ability to store magnetic energy, and $\mu''$ is the imaginary part representing loss. Since both $\epsilon$ and $\mu$ can slow an electromagnetic wave, and both increase on a per unit volume basis with compaction, the permeability could play a role in the measurement of the asphalt density, but only if a substantial magnetic field H exists in the material. Likewise, $\epsilon''$ and $\mu''$ will increase the energy loss with compaction. It has been suggested to add lossy ferrite oxides to an asphalt mix in order to increase the efficiency of microwave heating. The asphalt can be heated during application to maintain temperature, or during repairs or removal.

Referring to FIG. 1, one method of measuring real and imaginary parts of permittivity is defined by ASTM Standard D2520-95, which is hereby incorporated by reference. The test method of D2520 is based on microwave measurement of the complex scattering (S) parameters throughout a specimen in a resonant transmission line or closed cavity. In this technique, the sample is placed inside a transmission line or cavity and is the device under test (DUT) 10. The methods herein incorporate these teachings and further can be extended to leaky type resonators. The measurements may be implemented by a network analyzer 20 analyzing the wave propagation through the material specimen using S-parameter analysis. They can be implemented also by analyzing the wave propagation through a transmission line or waveguide and interacting with the material at the boundary of the sensor.

S-parameter analysis techniques may be accomplished by a variety of commercially available broadband network analyzers, such as the HP (Agilent) 8753 Network Analyzer manufactured by Agilent Technologies, Inc. of Palo Alto, Calif., as shown in FIG. 1. Network analyzers 20 are well known to those of ordinary skill in the art for measuring the voltage standing wave ratio, complex reflection/transmission coefficients, impedance and admittance matrix parameters, and return and insertion loss of a device under test. The setup typically includes the network analyzer 20, a transmission/reflection test set 22, and the device under test 10, which is described in various embodiments below. These instruments are capable of both frequency and time domain analysis. The conversion between these two domains is accomplished using the Fast Fourier Transform commonly known as the FFT. For example, an impulse or step response can be analyzed for dispersion and group velocity. The velocity is inversely related to the real part of the dielectric constant and in fact proportional to $1/\sqrt{\epsilon'}$ (to) whereas the loss is related to the imaginary part $\epsilon''(\omega)$. Hence, both the real and imaginary parts can be frequency dependent, as one skilled in the art would know. These days it is now possible to economically build and design one port and full two port network analyzers that are compact and efficient on battery power.

Figure 2:
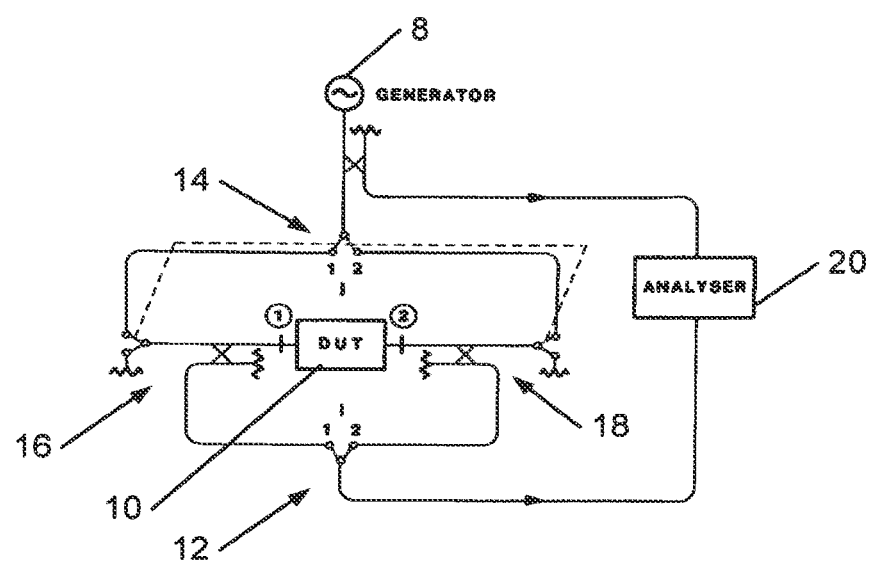
FIG. 2 is a diagram of an apparatus for obtaining the density of a pavement material according to one embodiment of the invention.

FIG. 2 is a simplified diagram of a network analyzer 20, including a frequency generator 8, illustrating the switching network 12, 14 and directional couplers 16, 18 for a full two port system to a DUT 10. There are many designs that could be used for the network analysis including scaler and vector network analyzers, some use simple diode detectors as can be found in publications like "Microwave Impedance Measurement by P. I. Somlo, BS J. D. Hunter, Peter Peregrinus Lt., London UK. 1985, or Microwave Measurement Edited by A. e. Bailey, Peter Peregrinus Lt., London UK. 1985. Reflectometers, VSWR bridges, and network analyzers can be based on bridge circuitry for lower frequencies, and couplers for the higher frequencies.

Impedance, permittivity, permeability, complex permittivity, and complex permeability of a material can be measured using S-parameter analysis, such as described in Agilent AN 154 S-parameter Design Application Note, which is hereby incorporated by reference. As S-parameters relate ratios of RF network inputs to outputs, they can be used to measure the ratios of RF network inputs and outputs for a material placed within a closed chamber or near an open sensor system. An incident RF electromagnetic wave is actively excited and the system responds according to the boundary conditions and constitutive relations of the material. For example, $S_{11}$ is a reflection measurement from the device under test that may yield return loss. $S_{12}$ is a transmission measurement through the device under test that may yield insertion loss. As such, $S_{11}$ and $S_{12}$ may be measured as a ratio of the RF input and output, in magnitude and phase. Hence these embodiments of the invention employ a measuring system comprising a wideband microwave sensor for exciting the DUT, a coupler, and a measuring circuit allowing scattering (S) parameters, impedance (Z) matrix parameters, or admittance matrix (Y) parameters and a data processing unit with display and software. From these, calculations of stored energy in a near field, parameters such as propagation constants α, β, resonant frequency and Q, and phase and group velocity can be deduced. From these (not limited to these specifically) a resulting property of the sample is found. The system uses a microwave sweeping oscillator to permit measuring the parameters such as the scattering parameters and other matrix parameters as a function of frequency, such as to locate a resonant frequency, Q, maximum or minimum of $S_{11}$ or $S_{21}$ as a function of frequency. The display and software could be integrated into a single unit much like a Troxler 3440 Nuclear gauge. This instrument incorporates downhole as well as surface measurements. The processing unit and display could be linked to a PDA using a wire or wireless connection. The software would include all the basic commands in addition to project management programs.

While material measurements have been described in conjunction with network analyzers to determine parameters such as impedance, permittivity, permeability, complex permittivity, and complex permeability by using S-parameters, it will be understood by those of ordinary skill in the art that other measurement systems utilizing other material analysis techniques may be used in conjunction with these methods and the device under test described herein. In fact, any electromagnetic wave analysis procedures that permit determinations of permittivity and complex permittivity either via software or manual methods, may be implemented in conjunction with the present invention without departing form the spirit or scope of the claims.

Resonant Cavity Sample Gauge

In the asphalt pavement construction industry, the cylindrical asphalt core is a common sample geometry. Accordingly, asphalt cylinders may advantageously be used in a resonant cavity to determine permittivity properties. According to one embodiment of a method of determining the density of an asphalt sample, the permittivity analysis may yield density measurements. These results could be used to calibrate field instruments. It should be noted that while a rectangular resonant cavity is described below as an appropriate measurement device for an asphalt sample, other resonant devices are known to those of ordinary skill in the art and may be substituted accordingly. Other waveguide resonators include cylindrical, reentrant, Fabry Perot, or the devices made from microstrip, slotline, coplanar waveguide, coplanar strips, surface waveguide, dielectric resonator and any of a number of resonating structures and modes such as TEM, quasi-TEM, TE, TM, or hybrid HE modes. The measurements could be made in the reflection mode, transmission mode or combinations thereof. The structures could have loads to satisfy certain boundary conditions such as open, short, match, or even a resonant load such as a short or resonant dipole. Here, the dipole would react with the near field and the impedance would shift the resonant frequency of the feed. These could be realized using a microstrip patch antenna, or even an antenna array, such as described in "A New Method of Measuring Dielectric Constant Using the Resonant Frequency of a Patch Antenna", Du Shimin, IEEE Transactions of Microwave Theory and Techniques, No. 9, September 1996. In any event, the microwave radiation will interact in the near field with the material under test for contact devices, and in the far field for non-contact devices or deeper measurements.

As described herein, it should also be noted that the sample is not necessarily small compared to a wavelength, but asphalt samples have a dielectric constant typically less than about 8 and are constant in shape. As such, a constant shape of both calibration samples and measured samples permits shape error to be corrected. The large size of the sample, as compared to the wavelength, can be corrected for with a correction factor K. The correction factor may be found using a finite element analysis or any number of numerical computational techniques, discussed in more detail below. If it is a common shape such as a small cube or rod it is possible to obtain corrections using rigorous mathematics with appropriate boundary conditions, but in general, the Finite Element or other numerical techniques are useful for any geometry. Other numerical techniques include finite difference, finite difference time domain, method of moments, etc. Therefore, the ability to disregard shape, the ability to correct for size, and the relatively low dielectric constant permits perturbation techniques or in general "wave like propagation" methods to be used to measure the permittivity of asphalt samples or surfaces. The sensors can be used for spot checking an asphalt or soil surface, or a surface wave could be launched and detected covering larger areas. It is well known that a surface wave has a penetration depth inversely proportional to the frequency of excitation. This device could be a slow wave structure such as a corrugated slab in contact with the medium of interest. The propagation constant as a function of frequency could then yield information of the quality vs. depth.

Figure 3:
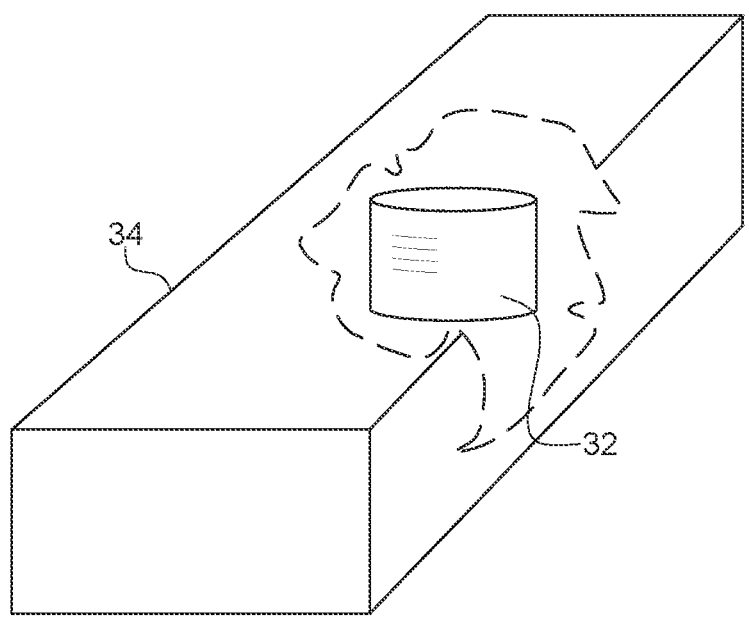
FIG. 3 is a resonant cavity waveguide including a material sample employed for obtaining the density of a pavement material according to one embodiment of the invention.

The following illustrates one method according to one embodiment of the invention for obtaining the density of an asphalt sample from a permittivity analysis. Referring now to FIG. 3, a rectangular $TE_{101}$ mode resonant cavity 32, which is may be one embodiment of the DUT in FIG. 1, was used to obtain measurements of an asphalt sample 34. This rectangular resonant cavity has dimensions of 0.9×0.4×0.19 meters. ASTM standard D-2520 is a standard for small samples that meet certain boundary conditions that may be employed with boundary value modifications. In the standard, the sample is presumed to be thin and extends all the way through the cavity. Such a sample allows for easy solutions of Maxwell's Equations and the necessary energy analysis. First, the small sample does not "perturb the fields" hence you can assume that the field configuration is exactly the same before and after insertion. Furthermore you can calculate the fields of the empty cavity, and use the same solutions for the loaded cavity. Also, with this setup and mode, the sample is always tangent to the fields and there are no perpendicular fields interacting with the sample. This assures that the field in the sample is exactly the same as with the empty cavity.

In FIG. 3, however, there is a large sample 32 that sits in the bottom of the cavity 34. From boundary conditions the field inside the sample will be different from the empty cavity, as we have normal components. Also since the sample 32 is about 0.15 m wide and 0.1 m tall it is no longer electrically small compared to a wavelength. So the ASTM boundary conditions do not apply if the sample does not extend fully from top to bottom, or was not always tangent to the electric field. It would be convenient to have air gaps between the cavity 34 and the sample 32 so that it inserted easily, and this would require some correction as well.

For an empty, air filled, rectangular cavity the resonant frequency is found by solving Maxwell's Equations with the appropriate boundary conditions, so every resonant structure will have its own unique relationship for resonant frequency.

The fundamental mode for the rectangular cavity is $$f_{101} = \frac{c}{2\pi\sqrt{\mu_0\varepsilon_0}}\sqrt{\left(\frac{\pi}{\text{width}}\right)^2 + \left(\frac{\pi}{\text{length}}\right)^2} \quad (1)$$

For this example cavity 32, the empty resonant frequency is approximately 428 MHz. It is known from perturbation theory that $$\frac{\partial f}{f} = \frac{f_2 - f_1}{f_2} + \frac{j}{2}\left(\frac{1}{Q_2} - \frac{1}{Q_1}\right) = -\frac{(\varepsilon_r - 1)}{2}\frac{\int_{V_{Sample}}|E_1 \cdot E_2|^2 dv}{\int_{V_{Cavity}}|E_1|^2 dv} \quad (2)$$

(See R. F. Harrington, "Time Harmonic Electromagnetic Fields", McGraw Hill Book Co., 1961.) Where $E_1$, $f_1$ and $Q_1$ are the electric field, frequency and quality factor for the empty cavity and $E_2$, $f_2$ and $Q_2$ are for the cavity containing the sample 34, while $V_{cavity}$ and $V_{sample}$ are the volumes of the cavity 32 and sample respectively. The quality factor Q is the ratio of energy stored in the system to that which is dissipated per cycle. For a transmission type resonator, it is measured using the 3 db bandwidth and the resonant frequency of the configuration. The quality factor is defined for any resonant system whether it is a waveguide cavity, a microstrip resonator, a resonant transmission line or a cavity backed antenna.

For an unperturbed $TE_{101}$ mode cavity the electric field intensity, E, is $$E_y = E_0 \sin\frac{\pi x}{a} \sin\frac{\pi z}{d} \quad (3)$$

where a is the width of the cavity and d the length in meters.

Assuming for small samples that $E_1 = E_2$, Equation 3 may be substituted into Equation 2 resulting in the solution for real and imaginary parts of permittivity, as:

$$\frac{f_2 - f_1}{f_2} + \frac{j}{2}\left(\frac{1}{Q_2} - \frac{1}{Q_1}\right) = -\frac{\varepsilon' - 1 - \varepsilon''}{2}\left(\frac{4V_{sample}}{V_{cavity}}\right) \quad (4)$$

Such that $$\varepsilon' = \frac{f_1 - f_2}{2f_2K}\frac{V_{cavity}}{V_{sample}} + 1 \quad (5)$$

$$\varepsilon'' = \frac{1}{4}\frac{V_{cavity}}{V_{sample}K^2}\left(\frac{1}{Q_2} - \frac{1}{Q_1}\right) = \sigma/\omega\varepsilon_0 \quad (6)$$

where σ represents the conductivity of the asphalt sample and K is the geometrical correction factor and accounts for the change in the electromagnetic fields with shape, permittivity and orientation. For a small sample whereby the tangential E field is continuous across the boundary and throughout the sample K=1. However, for larger samples or samples not oriented parallel with the fields, K must be determined by closed form or using a numerical method such as finite element analysis. In general, the electric field $E_2$ is only found in context with the knowledge of the sample geometry, material properties and field orientation. The sensitivity is maximized when the E field is parallel to the sample boundary, but the analysis works for normal fields or combinations thereof.

The finite element analysis requires modeling a "virtual" sample having known dielectric properties and dimensions. The analysis therefore yields the complex frequency response of the system. For example, the complex propagation constant, resonant frequency and loss effects can be obtained. The finite element results may then be compared to actual measurements, and the parameters in the finite element model adjusted until the model produces exactly the same results as the measurements over a bandwidth. Hence, a solution to the material parameters is indirectly found. This is computationally extensive, and could require hours to find a solution.

In another approach, curves of resonant frequency or loss vs. permittivity and sample dimension could be found using the computational techniques and stored in a computer. Then in the portable device, the sample dimensions could be entered into the computer along with the loss and frequency results, and the complex permittivity could be found. Still, if the sample geometries are of standard shape as in the asphalt industry, correction factors to closed form equations can be obtained as is the case of Equations 5 and 6. The correction factors could also be obtained experimentally if one possesses standard materials of known permittivity and constant geometry from sample to sample to use for calibration. It was found that the correction factor for larger samples could be used for smaller samples of the same general shape.

Typically, when a sample dimension is less than about $\lambda/10$ it can be considered electrically small. In these experiments, the pucks are usually about 150 mm in diameter, and 115 mm high. In the rectangular wave-guide used in these experiments, the first mode resonated at about 426 MHz in air with a wavelength of about 750 mm. So the sample is not considered small, and furthermore, it does not extend to the top of the wave-guide. This gap between the sample and the wave-guide roof is a normal E field boundary condition, which will substantially change the fields in this region for $\varepsilon_r > 1$. This will further remove the solution from the ideal case.

Figure 4:
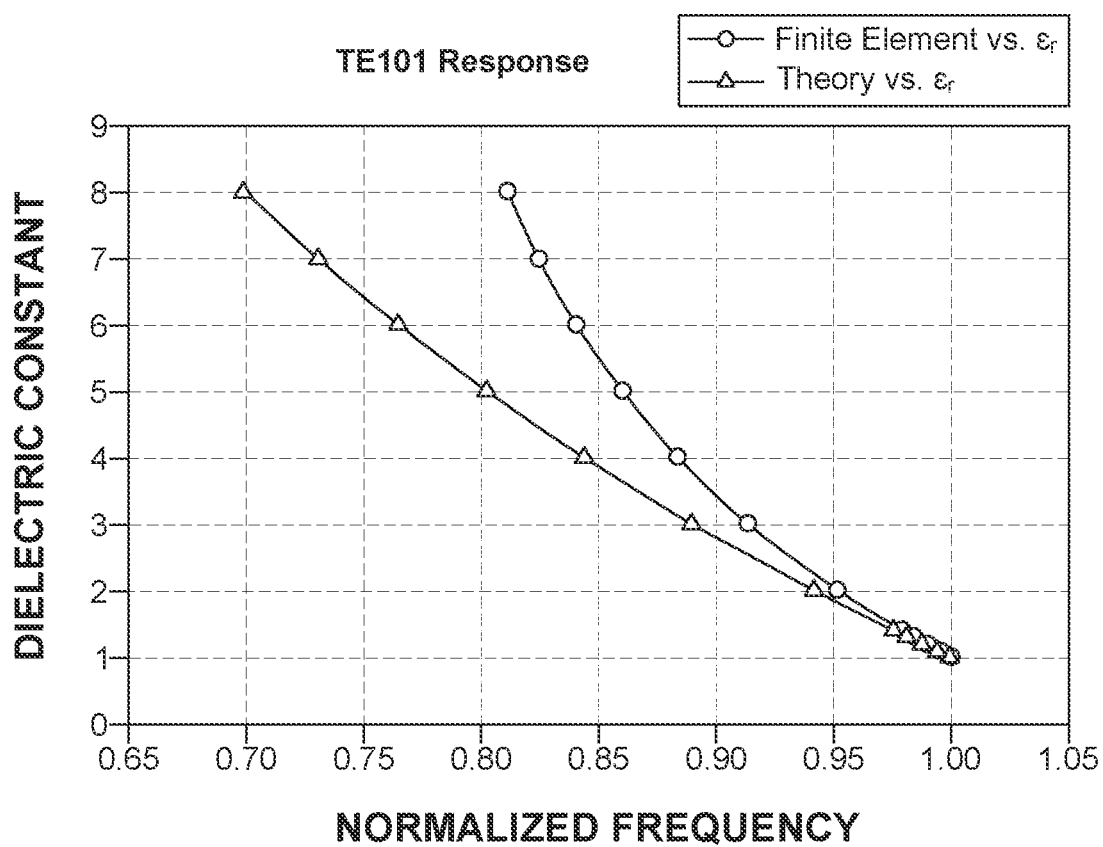
FIG. 4 is a plot of finite element analysis and theoretical solution of the cavity and sample of FIG. 3 according to methods of one embodiment of the invention.

The difference between the ideal solution and the FEM solution with the short sample puck of material is illustrated in FIG. 4. A finite element simulation was carried out using a rectangular cavity of the dimensions 0.9144×0.1905× 0.3794 m. Inside the cavity and placed at the point of maximum electric field (the center for the fundamental mode) was a virtual cylindrical puck with a radius of 75.057 mm and a height of 115 mm. In the numerical analysis, the permittivity was changed from 1 to 8. For an air filled cavity, it was found that the numerical analysis gave a resonant frequency $f_1$=427.6 MHz. With some adjustment of the magnetic loop coupling mechanism this agreed exactly with the actual measured value. The program was then run with the different permittivities, and each time the Eigen-frequencies were recorded. The frequencies are shown in columns 4 and 5 of Table 1 below.

TABLE 1

| $\varepsilon_r'$ | $\delta f/f_1$ (theory d << λ, K = 1) | $\delta f/f_1$ (Finite elements) | $f_1$ (Finite Element) | $f_1$ (theory) K = 1 |
|---|---|---|---|---|
| 1.0 | 0 | 0 | 427.6 Mhz | 427.6 Mhz |
| 1.1 | .00616 | .00538 | 425.31 | 424.98 |

TABLE 1-continued

| $\epsilon_r'$ | $\delta f/f_1$ (theory d << λ, K = 1) | $\delta f/f_1$ (Finite elements) | $f_1$ (Finite Element) | $f_1$ (theory) K = 1 |
|---|---|---|---|---|
| 1.2 | .0123 | .0107 | 423.08 | 422.40 |
| 1.3 | .0185 | .0159 | 420.89 | 419.83 |
| 1.4 | .0246 | .0211 | 418.75 | 417.33 |
| 1.5 | .0308 | .0263 | 416.65 | 414.82 |
| 2 | .06158 | .0508 | 406.94 | 402.8 |
| 3 | .1232 | .0944 | 390.70 | 380.70 |
| 4 | .1848 | .1315 | 377.92 | 360.90 |
| 5 | .2463 | .1628 | 637.72 | 343.10 |
| 6 | .3079 | .1896 | 359.44 | 326.94 |
| 7 | .3695 | .2127 | 352.60 | 312.23 |
| 8 | .4311 | .2327 | 346.89 | 298.79 |

Figure 5:
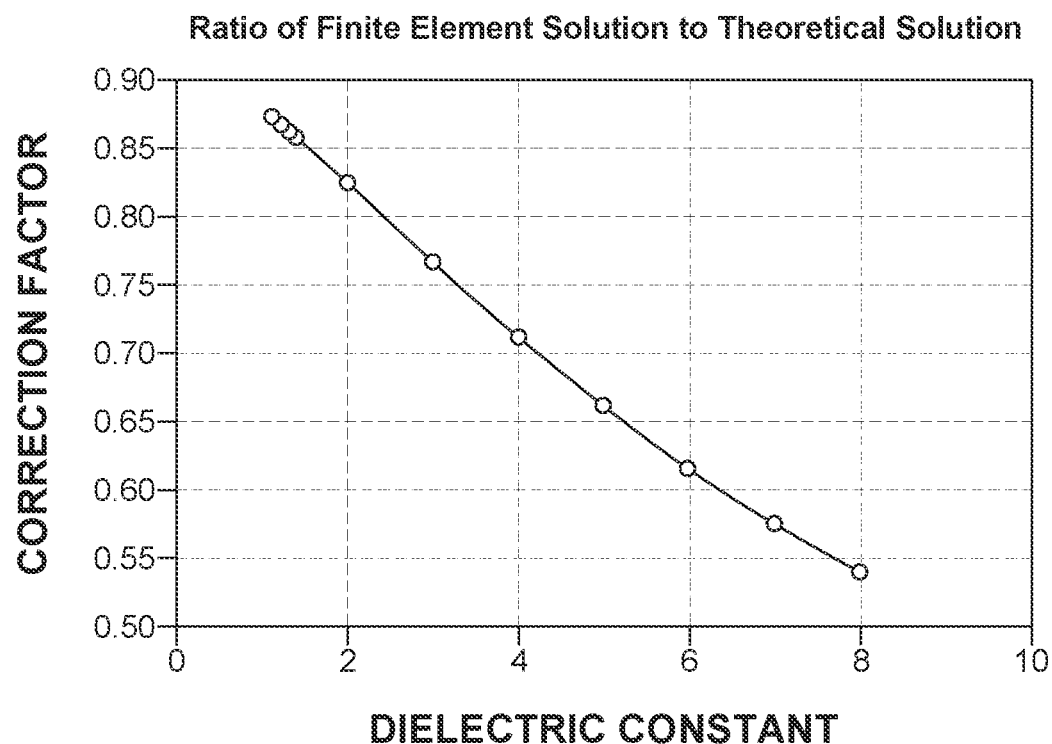
FIG. 5 is a ratio, K, of the finite element analysis for correction to the theoretical solution as a function of dielectric constant according to methods of one embodiment of the invention.

In Table 1 $\delta f = f_1 - f_2$ and the "theory" columns refer to the use of Equations 5 and 6 with K=1. The correction factor K can be found for each sample by simply dividing column 3 by column 2. FIG. 5 is a plot of K vs. Cr for this geometry. In equation form, the correction factor was found to be $$K = 0.0477 + 0.9 \cdot \exp(-0.076 \epsilon_r) \quad (6b)$$

Figure 6:
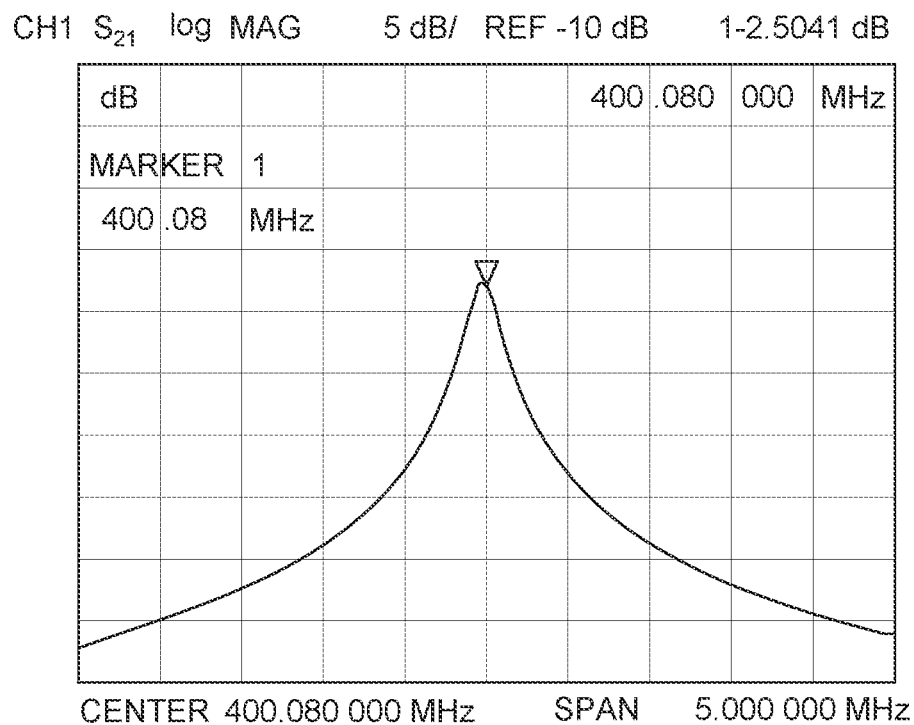
FIG. 6 is a plot of frequency sweep of the cavity of FIG. 3 and a sample illustrating the resonant frequency.

As an example using the real part of the permittivity, a calibration sample was inserted into the cavity. In one example, the calibration sample was a polyethylene puck of radius 74.95 m, height of 114.5 mm and permittivity of 2.6 The frequency was swept over the proper band for the first resonance and is shown in FIG. 6. Here we see that the resonant frequency is 400.08 MHz. Substituting this into Equation 5 with K=1 yields a dielectric constant of $$\epsilon_r = 1 + (66.09/2.021)(427.6 - 400.08)/(2 \cdot 400.08)$$

or $\epsilon_r = 2.09$. Multiplying this by K found from (6b) results in a value of 2.57. Notice that the height of the polyethylene cylinder was not exactly the same as that which was used in the FE simulation. As long as the measurement geometry is relatively close to the simulation, good results can be obtained. For larger differences in height h, a correction for the permittivity can be estimated using $$\epsilon_r = (\epsilon_r - 1) h / 115 + 1 \quad (6c)$$

This is derived using the fact that the frequency shift is proportional to the ratio of volumes of the sample and the cavity Vs/Vc.

As a test incorporating the imaginary part of the permittivity it is known that DELRIN, a well-known plastic, has a complex permittivity of 3.1+j0.148. First a small sample was simulated using the finite element program. This sample extended from the floor to the ceiling of the cavity and was only 25.4 mm in diameter. This gave a sample volume of 96.528e-3 m$^3$. Since the electric field vectors are always parallel to the sample, and the sample is small compared to a wavelength, K=1. Equation (5) and (6) gives a resonant frequency of 424.99 Mhz and a Q of 1104. As a check of the numerical program, this material was coded up and it was found that the Finite element analysis yields f=424.94 Mhz and a Q of 1056. A near perfect agreement. Next in the model, the Delrin was expanded in size to have a radius of 75.057 mm and shortened to a height of 115.0 mm leaving a substantial air gap between the sample and the cavity ceiling. According to Table 1, this would result in a K of 0.7666. Incorporating K into (5) and (6), and backsolving for frequency we find $f_2$=389.21 Mhz. Likewise, Equation (6) results in a quality of 93.1, both agreeing well with the numerical analysis. Therefore, it was concluded that even with large samples, the geometrical correction factor derived only from the real part of the permittivity could also be used for the imaginary calculations, and in fact, could be absorbed into the shape factor.

To summarize, for the above described cavity, FIG. 4 illustrates the TE$_{101}$ response for a finite element analysis in comparison to the typical ASTM 2520 method where the field E is not perturbed by the insertion of the sample. FIG. 5, illustrates the correction factor K as a function of dielectric constant. Furthermore, during the course of the analysis it was observed that the correction factors for both loss and frequency shift (thus real and imaginary permittivity) were very close. Therefore it deemed acceptable to assume the same correction factor for both the real part and the imaginary part of the permittivity. As such, the absolute permittivity of the sample may be determined from the above equations; even for electrically large and odd shaped samples.

For circuits, the quality measurements require correction for impedance loading and loss other than from the sample properties and measurements. For an unloaded device, $$\frac{1}{Q_{L1}} = \frac{1}{Q_0} + \frac{1}{Q_E} \quad (7)$$

where $Q_{L1}$ represents the total sum of all losses, $Q_O$ is the internal energy loss, and $Q_E$ is the external energy loss through the coaxial cable and network analyzer. For a device loaded with a sample, $$\frac{1}{Q_{L2}} = \frac{1}{Q_0} + \frac{1}{Q_E} + \frac{1}{Q_S} \quad (8)$$

Accordingly, the sample Q may be determined by $$\frac{1}{Q_{L1}} - \frac{1}{Q_{L2}} = \frac{1}{Q_S} \quad (9)$$

For all three loss mechanisms, the loss equation is $$Q_L = \frac{\omega L}{R_S + R_{sample} + Z_0} \quad (10)$$

where $R_s$ represents internal losses for example the surface resistance of the resonator, $R_{sample}$ represents the loss of the sample, and $Z_O$ represents the impedance of the coaxial cable or possibly other external losses such as radiation. At resonance, a coupling factor, β, relates $Q_O$ and $Q_L$ [R. E. Collin "Foundations for Microwave Engineering", McGraw Hill, 1966.]

$$Q_O = Q_L (1 + \beta) \quad (11)$$

wherein β is either overcoupled, $$\beta = R'/Z_O \quad (12)$$

undercoupled, $$\beta = Z_O/R' \quad (13)$$

or critically coupled.

$$\beta = 1 \quad (14)$$

It is therefore advantageous to undercouple such that $\beta \ll 1$, to approximate $$Q_L = Q_S \quad (16)$$

To summarize, the purpose of the cavity measurements of a calibration sample is to obtain the complex permittivity of mix materials for calibration of field devices, and to obtain these properties for laboratory records of the engineering properties of cores. The engineering properties are related to the quality of the cores through the chemistry of the binder (oxidation), water and void content of the cores.

Now when the permittivity of the asphalt sample has been established, the cavity can be calibrated with multiple asphalt samples of a known density. For example, at least two samples of different density but of the same mix (permittivity characteristics) are placed in the resonator to obtain measurements of $\Delta f$ or $\Delta Q$ resulting in a linear equation for density. However, since most mixes have similar slopes, a generic calibration curve could be obtained by finding only an offset of the calibration curve. Here, only one asphalt sample of particular permittivity and known density would be needed.

The simple model incorporated the dimensions of the puck, and a variable permittivity. The different mixes have different "base" permittivities that are reduced by the increase in air voids, as the density decreases.

Density Relations

As the material is compacted, the dipole density increases and thus both $\epsilon'$ and $\epsilon''$ will increase. These increases will decrease the phase velocity of the electromagnetic wave, and increase the insertion and return loss of the system. For a resonant structure, both the resonant frequency and the Q will decrease with increasing compaction. Off resonance, the magnitude and phase of the reflection and transmission coefficients will change in accordance with the characteristics and length of the waveguiding structure, in this example a resonant cavity. As a result, it is possible to measure density increases using $\epsilon'$ and/or $\epsilon''$ increases, or decreases in f and/or Q. With these types of measurements, a calibration using calibration samples of known densities and consistent shape is necessary. If the calibration is performed using SUPERPAVE type asphalt cores of radius about 75 mm and heights near 115 mm vs. f and Q, then the calibration curves will be restricted to these shapes and sizes; except for some height variation that could be corrected using (6c). In other words, the smaller Marshall pills could not be used without a separate calibration, as their radius is about 50 mm. On the other hand, if the density calibrations are defined using the complex permittivity, then no matter what the shape of the sample, the calibration will hold once the permittivity of the sample is measured.

Shape independent calibrations can be incorporated by taking the ratio of Equations (5) and the square root of (6) such as described in U.S. Pat. No. 5,554,935. Incorporating the fact that $V_s$=mass/$\rho$ where $\rho$ is the bulk density we find $$\rho = (G/(\epsilon_f \sqrt{Q})) + C^2 \quad (6d)$$

where C is a constant. With this approach, frequency and Q can be used with the same calibration equation for different shapes.

Frequency Only Calibration 37 cores were produced in a Gyratory compactor. These were of the species of limestone and granite. There were 6 series of cores. With each series, three different void ratios were targeted in the mix by varying the mass of the materials for a particular compaction height. The height was near 115 mm just like the simulations, and there were two duplicates for each density.

In the cavity, two measurements were obtained for each core characterized by flipping the sample upside down. So each series had 6 measurements. In the cavity, the sample is inserted and the frequency shifts down from the empty 426.7 MHz value. Analysis at multiple frequencies is desirable and could be obtained by selecting higher order modes or designing a different cavity.

From the finite element analysis, an equation was derived that directly relates the resonant frequency to the permittivity and $$\epsilon' = -0.7690 + 7355.34 \exp(-0.0194 f)$$

where f is in MHz. Since the frequency shift is directly related to the ratio of volumes Vs/Vc, then for different sample heights a correction for the permittivity can be estimated using Equation (6c). These relationships were used to find the real part of the dielectric constants of the cores made in the laboratory. The results were then used to obtain equations relating the permittivity to the density. The densities of the cores were obtained using nuclear instruments and measuring methods.

As an example, consider the series 2-xxx cores. For the core 2-102, the frequency easily converts to a dielectric constant. The measurement results are shown in Table 2 below where height correction was incorporated using 6c. The X and O represent measurements whereby the core was physically flipped in the cavity.

TABLE 2

| Freq | S21 | DeltaF | QL | | |
|---|---|---|---|---|---|
| X | | | | | |
| 368.5625 | −19.4509 | 0.72594 | 507.701 | | |
| O | | | | | |
| 368.3375 | −19.8601 | 0.76284 | 482.8496 | | |
| Sample ID | Height mm | AVG (gmb) | PCF (nuclear) | mass (g) | PCF (X) Microwave |
| 2-102 | 113.900 | 2.032 | 126.472 | 4102.9 | 126.291 |
| Freq | S21 | | DeltaF | QL | |
| 368.5625 | −19.4509 | | 0.72594 | 507.701 | |
| epsX | epps X | fact | epsO | eppsO | fact |
| 5.00 | 0.039064 | 0.639827 | 5.028544 | 0.041223 | 0.638667 |

For each different mix, a regression analysis was performed to obtain the calibration curve for that mix vs. the permittivity. Table 3 shows the results for series 2.

TABLE 3

| CORE | er' | er'' | PCF | slope | intercept |
|---|---|---|---|---|---|
| 2-102 | 5.042 | 0.039 | 126.472 | 17.444 | 38.340 |
| Flip core | 5.067 | 0.041 | 126.472 | 0.376 | 2.088841 |
| 2-103 | 5.058 | 0.035 | 126.196 | 0.994 | 0.570606 |
| | 5.067 | 0.039 | 126.196 | 2264.960 | 14.000 |
| 2-201 | 5.726 | 0.042 | 138.511 | 737.450 | 4.558272 |
| | 5.740 | 0.047 | 138.511 | | |
| 2-202 | 5.725 | 0.040 | 138.911 | | |
| | 5.728 | 0.042 | 138.911 | | |

TABLE 3-continued

| CORE | er' | er" | PCF | slope | intercept |
|---|---|---|---|---|---|
| 2-203 | 5.722 | 0.043 | 138.929 | | |
|  | 5.739 | 0.040 | 138.929 | | |
| 2-301 | 6.060 | 0.038 | 144.228 | | |
|  | 6.043 | 0.036 | 144.228 | | |
| 2-303 | 6.042 | 0.040 | 143.019 | | |
|  | 6.062 | 0.042 | 143.019 | | |
| 2-305 | 6.074 | 0.042 | 143.890 | | |
|  | 6.074 | 0.038 | 143.890 | | |

The residual is 0.994. A very good value representing a linear relationship between the microwave dielectric constant and the density of the cores.

Figure 7:
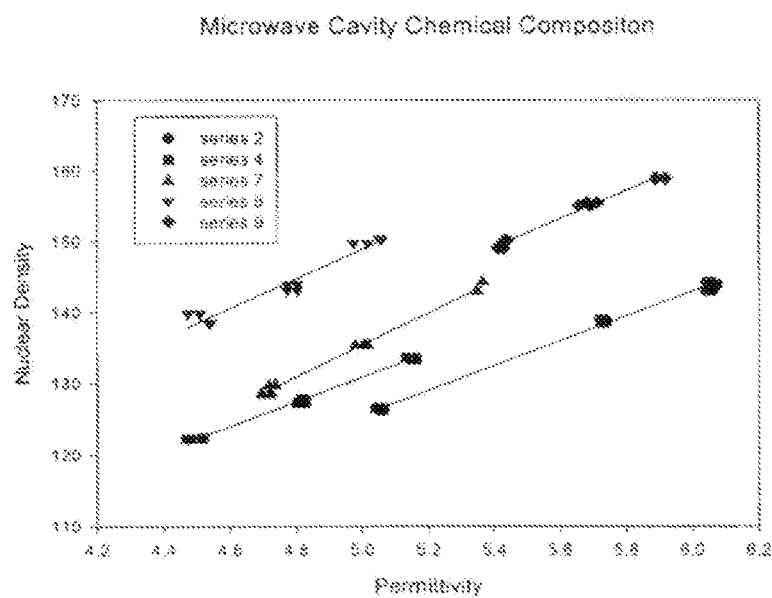
FIG. 7 is a plot of permittivities for a series of samples found employing methods according to one embodiment of the invention for a series of samples having known densities.
Figure 8:
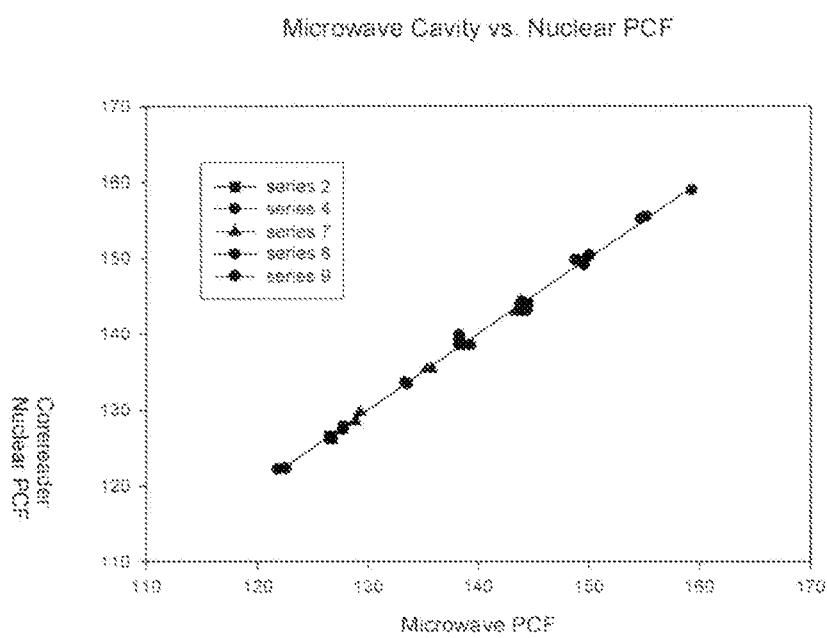
FIG. 8 is a plot of densities for a series of samples found according to methods of one embodiment of the invention compared to densities found by independent methods.

Note that $\delta f$ or $\delta Q$ can be used as a function of density, or $\epsilon'$ and/or $\epsilon''$ as a function of density. Alternatively, ratios of these parameters may be used such as $\epsilon'/\epsilon''$. An example is illustrated in FIG. 7 depicting $\epsilon'$. $\rho$ from the scattering coefficient ($S_{12}$) results of several different asphalt mixes. Note that FIG. 7 illustrates only the real part of permittivity. Also, each mix has different intercepts but similar slopes. Accordingly, it is acceptable to assume for these asphalt mixes that all of the curves may be approximated to a single slope and then only the intercept needs to be found. This approximation may assist to reduce field calibration steps, however, the preferred method is to offset both the slope and intercept. FIG. 8 illustrates the accuracy when each mix is calibrated for both slope and intercept.

For a single mix design, both $S_{11}$ and $S_{12}$ can be used to correlate between frequency shift and density, thus disregarding actual permittivity values in this case. In the field, measurements of the f and Q values or $S_{11}$ and $S_{12}$ can be easily correlated to the density of a test strip using cores or nuclear gauges without direct knowledge from the permittivity.

Reflection $S_{11}$

When a transmission line is terminated with a complex impedance, reflection measurements are appropriate. As is well known in the microwave analysis, the impedance is measured at a port, and the phase of this port (partly determined be the length from the device or load) defines the impedance in a predictable and cyclic manner. In particular, two common equivalent circuits can be obtained and are defined by the "detuned" resonance. One is the detuned short position, and the other is the detuned open position. Of course the equivalent circuit can take on an infinite number of impedances in between these extremes, but with proper referencing, the characteristics of the device can be extracted. Since the detuned short and open are mathematically dual to one another, the results of one can easily be carried to the other.

Figure 10:
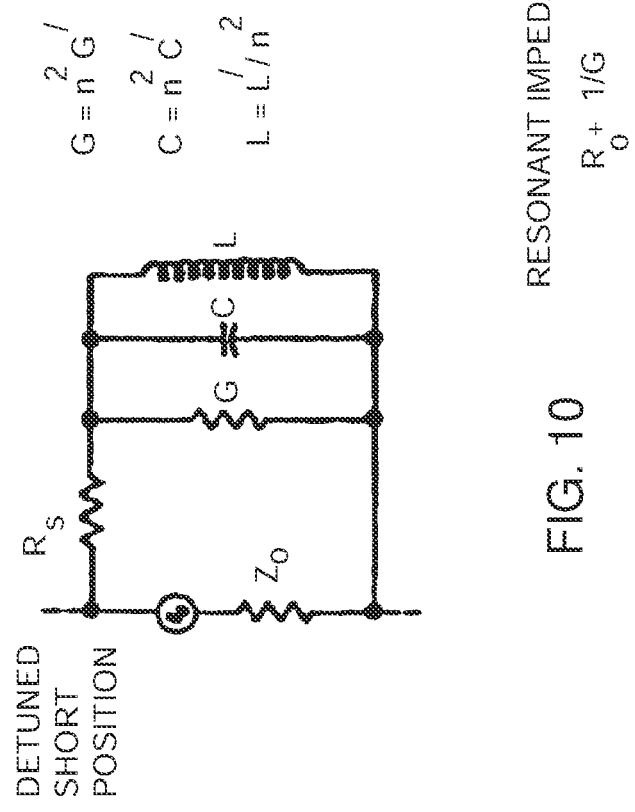
FIG. 10 is an electrical equivalent diagram of a detuned short microwave cavity according to one embodiment of the present invention.
Figure 9:
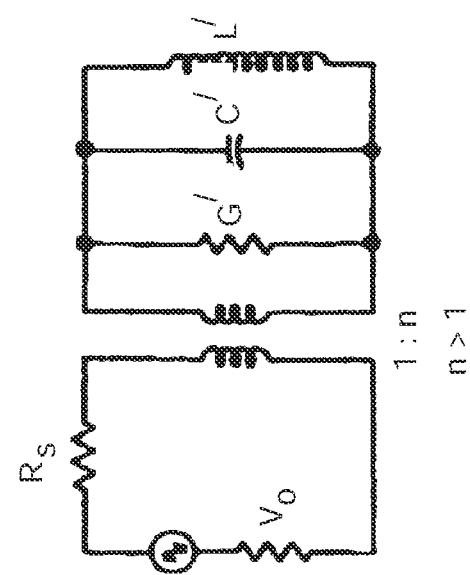
FIG. 9 is an electrical equivalent diagram of a tuned resonant cavity.

A tuned circuit is represented by FIG. 9 where a transmission line impedance $Z_O$, a coupling resistance Rs and the cavity loss G, and electric effect is C, and magnetic field effect is inductance L. The resonator as a detuned short circuit is shown in the FIG. 10, and the real and imaginary parts are proportional to the square of the coupling turns ratio n. Note that far off resonance, the circuit has the impedance of a short in the ideal case. This feature could be used to calibrate the systematic error of the network analyzer. For a microwave device, other resonances also effect the results. These models represent the response only near a particular harmonic. The impedance of the TE011 detuned cavity is shown in the following figure in a Smith Chart format, FIG. 12. Here the reference plane has been shifted to represent a short off resonance.

Figure 12:
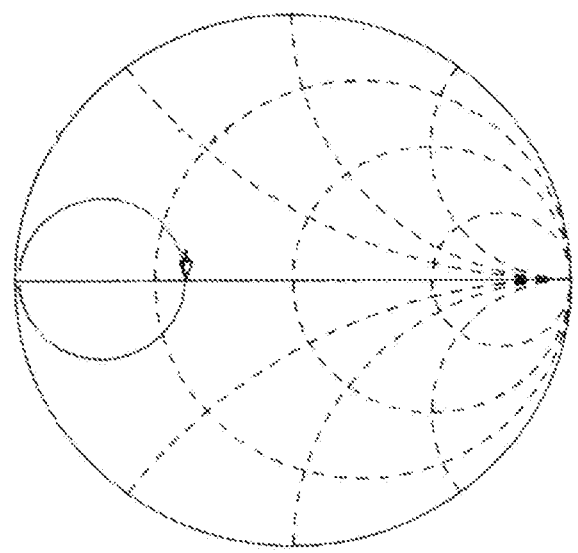
FIG. 12 is a smith chart plot of impedance of a cavity according to one embodiment of the present invention.

It should be noted that impedance plot 40 of FIG. 12 is nearly circular. Near the resonance, the resistance or loss is constant with frequency, and this loss is modeled as a constant resistance circle on the Smith Chart. At resonance, the impedance is real, and is closest to the center of the chart leading to a minimum VSWR. For a well matched device, the reflection coefficient in dB will have a very sharp dip making it easy to find the resonance frequency.

Figure 11:
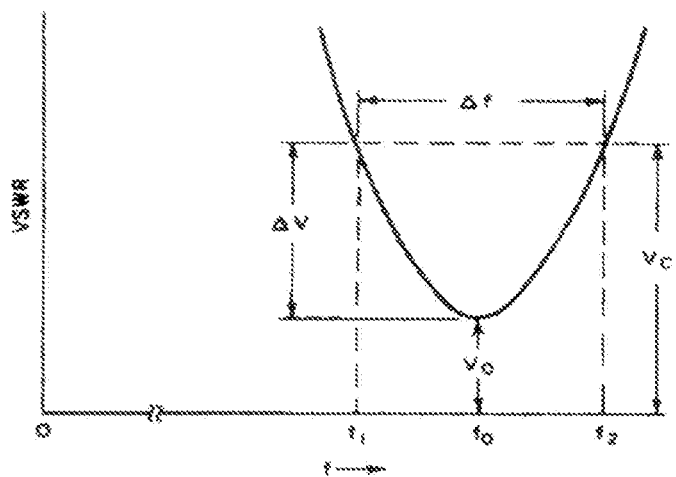
FIG. 11 is a plot of voltage standing wave ratio of a cavity according to one embodiment of the present invention.

A plot of VSWR near resonance is shown in FIG. 11. The procedure is to sweep the network analyzer over the pass band of the device and plot the VSWR as shown in FIG. 11.

For reflection measurements, the resonance corresponds to a minimum reflection coefficient or VSWR. As known in the art, it is also possible to obtain Q measurements using primarily reflection techniques. In this case, $\Delta f$ is found by the difference in frequency between the half power VSWR frequencies, such that $$VSWR_{\frac{1}{2}} = \frac{1 + S_0 + S_0^2 + (1 + S_0)\sqrt{1 + S_0^2}}{S_0} \qquad (17)$$

where $S_O$ is the VSWR at resonance with a sample in the cavity, and the 3 db power points correspond to $f_1$ and $f_2$ of the two $VSWR_{1/2}$ points.

When the system is undercoupled $$\beta = 1/S_O \qquad (18)$$

which is substituted to Equation 11, $Q_O = Q_L(1+\beta)$, since $$Q_L = \frac{f}{\Delta f} \qquad (19)$$

where $\Delta f$ is defined by the $VSWR_{1/2}$ above; $Q_O$ due to internal losses only can be found.

As will be recognized to one of ordinary skill in the art, then it is not necessarily the values of permittivity of the asphalt sample that are required to be calculated. Rather the density relationship may be compared to any number of parameters measured from the microwave transmission and reflection loss, frequency shifts, phase shifts, S parameters, admittance and impedance matrix parameters, etc. That is to say that the above simply describes one advantageous method to determine the density of the sample using the reflection and transmission measurements, while the measurements may be related in a number of other mathematically correct methods to the exclusion of having to solve for permittivity.

Figure 13:
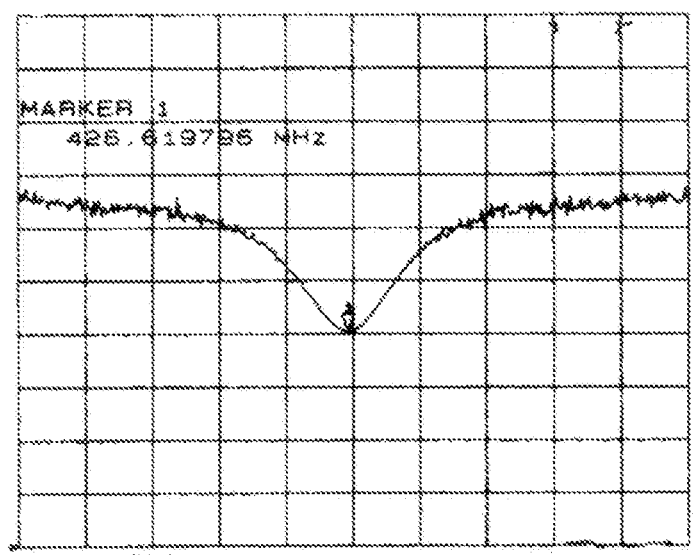
FIG. 13 is a plot of frequency sweep of a cavity and a sample illustrating the resonant frequency found according to methods of one embodiment of the invention.

The empty cavity in the reflection mode yielded an impedance plot 50 as a function of frequency shown in FIG. 12. Since $\beta<1$, the circle of constant resistance never crosses the center of the Smith Chart, and $\beta=1/VSWR=22.2/50=1/2.25$. An easy way to find the resonance is to plot the return loss or S11 in log magnitude and look for the minimum. This plot is shown in FIG. 13 and indicates that the frequency of resonance is 426.7 Mhz. The half power VSWR (Vc) is found to be 7.25, and this corresponds to a frequency bandwidth of about 285 Khz for a loaded Q of $Q_L=1497$, and the unloaded $Q_O=1.444*Q_L=2162$.

Samples were measured using the reflection method. A table of the results is shown below.

TABLE 4

| Sample | Frequency Mhz | VSWR | Ve | Bandwidth | QL | Qo |
|---|---|---|---|---|---|---|
| 2-102 | 368.23 | 27.79 | 57.63 | 849 Khz | 433 | |
| 2-202 | 362.3 | 64.94 | 131.9 | 874.5 | 414.35 | |
| 2-301 | 359.95 | 62.67 | 127.36 | 790.5 | 455.34 | |

Since these VSWR's were so high, the cavity was very much undercoupled, and the unloaded Q will be very close to the loaded Q's.

Figure 14:
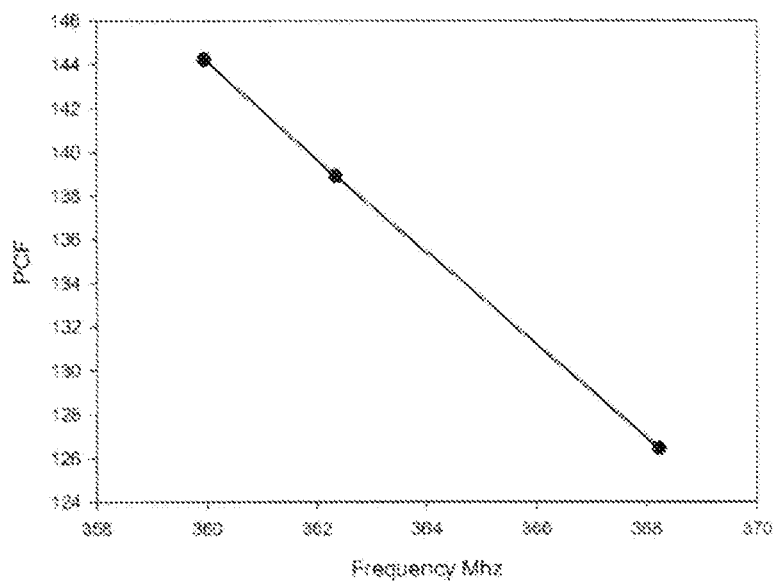
FIG. 14 is a plot of densities and resonant frequencies from different samples according to methods of one embodiment of the invention.

The resonant frequency can be plotted against the density of the cores for relative measurements as shown in FIG. 14.

$$PCF = 914.24 + f^* - 2.14, \ r^2 = 0.99988$$

Also, the dielectric constant can be calculated using the resonant frequency and the finite element model of the cavity and these results would be identically equal to the results obtained using the transmission cavity.

It is also notable that for microwave frequencies the calibration is less susceptible to change with the conductance due to moisture of a particular type of dielectric or pavement. Hence, calibrations may be more universal from mix to mix. In the microwave region, instead of measuring a lumped impedance, the reflection or transmission properties of the device are obtained. As for frequency dependence, the dispersion will be minimized as f increases as explained below.

For free polar molecules, the orientation and induced polarizations are a strong function of temperature; especially at relatively low frequencies. For moist (water containing) mixtures, $$\varepsilon_r = \varepsilon_{r\infty} + \frac{(\varepsilon_{rs} - \varepsilon_{r\infty})}{(1 + j\omega\tau)^\alpha}$$

where $\alpha$ is a correction for a distribution of relaxation times, $\tau$ is the relaxation time directly related to the mobility of the molecules, $\varepsilon_{r\infty}$, is the high frequency permittivity, and $\varepsilon_{rs}$ is the low frequency or static permittivity. At frequencies well above $1/\tau$, $\varepsilon_r = \varepsilon_{r\infty}$, $\varepsilon_{rs}$ decreases with rising temperature due to the increasing disorder in the molecules, and $\tau$ decreases with increasing temperature. By investigation of the dispersion of the real and imaginary parts of the permittivity from low frequencies to the microwave band, the moisture effects may be separated from other attributes such as porosity. For a heterogeneous mixture, these frequency effects will be exacerbated above any simple Debye effects as can be explained by the Maxwell-Wagner theory.

Since asphalt is a "binding" agent and is adsorbed into the aggregates, and since it is a large heavy molecule, the relaxation time is long resulting in relatively low dielectric constants and a low relaxation frequency. For this reason, microwave analysis of HMA is less susceptible to temperature variations when compared to the lower bands. Hence a wideband measurement swept through the microwave band can therefore result in the separation of moisture and density effects.

U.S. Pat. No. 6,414,497 and U.S. Published patent applications 20020175691 discuss the temperature effects of asphalt density measurements. In the microwave region, the temperature effects of polar molecules are negligible. However there will be temperature effects due to the simple volume expansion of the material under test. This is because the method of measurement is based on the dipole moment per unit volume of material. In this respect, slight temperature corrections to the microwave results could be useful for the most accurate results in quality assurance of paving materials. These linear corrections could be related to the base temperature of the asphalt. For instance, this expansion is confirmed by in ASTM standard D 4311-96, "Standard Practice for Determining Asphalt Volume Correction to a Base Temperature".

Microwave Planar Circuits

Figure 15:
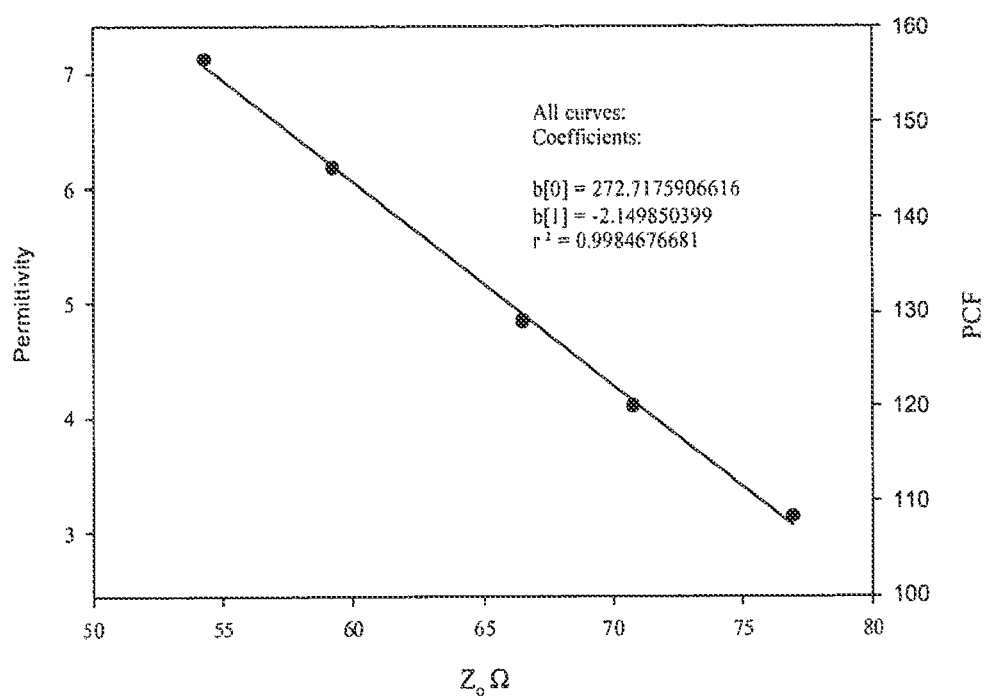
FIG. 15 is a plot of slotline impedance and density for a planar microwave circuit according to one embodiment of the present invention.

Microwave planar circuits may also be employed especially for use in non-destructive field tests of asphalt. Planar circuits are desirable because they include leaky fields configurable as dielectric sensors. FIG. 15 is a plot of slotline impedance vs. asphalt density in the microwave region, which illustrates that the complex propagation constant of microwave radiation can be detected using many different parameters such as complex resonant frequency, complex impedance, complex S parameters etc. The waveguiding or launching device can be microstrip, stripline, slotline, coplanar waveguide, circular waveguides, rectangular waveguides, or even open or leaky waveguides such as surface wave launching devices. A planar circuit can measure reflection coefficients or transmission coefficients. These responses are the direct result of the complex propagation constant in the surface of the asphalt and/or traveling across the surface of the asphalt as launched from a planar circuit. In microwave propagation, the resonator is just one means to measure the complex propagation constant $\alpha+j\beta$. The circuits mentioned above are a means to measure the complex propagation constant and S parameters through network analysis. The transmission line could also be loaded with a device that interacted with the material. The resulting impedance shift as a function of density could be detected at the input port through phase or resonance using network analysis.

Asphalt, in particular, is a complex molecule consisting of heteroatoms such as sulfur, nitrogen, and oxygen attached to the principle atoms of carbon and hydrogen. The resulting configurations are polar because of an imbalance of electrochemical forces in the bond. The asphaltenes are generally dark brown, friable solids and are the most complex components of the cement with the highest polarity. The remaining components are resins and oils.

Because the asphalt possesses a permanent dipole moment, and is a complex chemical, it will have a distribution of relaxation times leading to the Cole-Davidson equation $$\varepsilon_r = \varepsilon_{r\infty} + (\varepsilon_{rs} - \varepsilon_{r\infty})/(1+j\omega\tau)^\alpha - j\sigma/\omega\varepsilon_O$$

Where the "s" signifies the low frequency permittivity, and the $\infty$ signifies a high frequency permittivity. The last term is included to represent the losses from the carbon atoms or DC conductance. The frequency dependent term in the above equation is in the denominator, which also varies with the relaxation time $\tau$, the inverse of the relaxation frequency. So the mobility of the molecules or ability of the molecules to rotate is defined by the relaxation time, which also defines the "boundary" of the materials low and high frequency response. Since asphalt is a solid or semi-solid at room temperature, and is used as cement, it is understandable that the relaxation frequency will be low, and the permittivity will not be large as a result. In the mix, the asphalt is adsorbed onto the aggregate, which further "locks" the molecular movement. Typically the dielectric constants will be less than 7. When the asphalt is more liquid, the dipoles will rotate easier, increasing the relative permittivity. This is due the thermal breaking of the bonds. A measure of the strength of molecular binding is the energy released per mole when the bonds are formed. This is the activation energy Q. In general the dependence of the relaxation frequency on the activation energy and temperature is f∝exp(−αQ/T) where T is degrees Kelvin and α is a proportional constant. As T increases, the relaxation frequency follows.

Because the asphalt is a heterogeneous material which can be moist, there exist free ions and charges that can form on the particular aggregates. This leads to a Maxwell-Wagner effect whereby at the lower frequencies, extremely large permittivities are apparent. Since this is also a polar mechanism, this large "artificial" permittivity is also extremely frequency and temperature dependent. However, because of the reduced mobility or large relaxation time τ associated with this phenomenon, most of these effects are nonexistent in the VHF band and above. For moist soils, the dispersion can be extreme. A measure of the change in complex permittivity at microwave frequencies and below can lead to a measure of soil porosity.

Microstrip Surface Gauge

One microwave density device is the microstrip resonator that may be more practical in non-destructive field tests of asphalt. In this case the microstrip is an embodiment of the DUT from FIGS. 1 and 2. One such microstrip 60 is shown in FIG. 16(*a*). The microstrip line 60 is employed as a waveguiding device, and since it is an open structure, the fields extend into the space above the line. This is a desirable characteristic for a sensor. By increasing the thickness h, of the substrate 62, and decreasing the permittivity of the substrate 62, more of the field will propagate in the space above the strip as shown in FIG. 16(*a*). By coupling into the strip with an impedance discontinuity, the transmission line will resonate. For example, placing a material 64 (FIG. 16(*b*)) of higher dielectric constant in the space adjacent the line, even more of the energy will exist in the material 64. This is referred to as inverted microstrip, and as the dielectric constant of the material 64 is increased, the phase velocity will decrease, and the resonator will decrease its resonant frequency.

Much like the method employed above in conjunction with the cavity resonator, the Q and resonant frequency can be measured by the network analyzer and the effective permittivity ε'−jε" can be found. Note that in FIG. 16(*b*), the asphalt would act as the upper dielectric layer. In one useful embodiment the microstrip is a meander line microstrip 66, as illustrated in view of FIG. 16. Ring resonators are very convenient geometries as well. In these examples, the transmission lines were operated as two port structures. However one port devices can also be used such as a resonant "cavity backed dipole." The resonance may be exclusively the dipole, or a slot antenna excited by microstrip. It may also be a cavity backed slot antenna or the result of a tuned short dipole/transmission line circuit.

The microstrip resonator operates in the same principle as the waveguide resonator with a few significant differences. Like the cavity, the shift in frequency can be measured and the $Q_L$ value is $$Q_L = \frac{f}{\Delta f} \tag{20}$$

Where $\Delta f$ is usually defined by the −3 dB frequency values off maximum of S21. Using an effective real permittivity for the measurement volume of the resonator (a portion of the field fills the resonator), the imaginary part of the permittivity is $$\varepsilon''_{re} = \frac{\varepsilon'_{re}}{Q_{Asphalt}} \tag{21}$$

As resonance occurs approximately when $$L = n\frac{\lambda_g}{2} \tag{22}$$

and $$\frac{c}{\sqrt{\varepsilon_{re}}} = f\lambda_g \tag{23}$$

Then at the second harmonic, n=2, $$\varepsilon'_{re} = \left(\frac{c}{fL}\right)^2 \tag{24}$$

It is also a reasonable assumption that $$\frac{1}{Q_{Asphalt}} = \frac{1}{Q_{L2}} - \frac{1}{Q_{air}} \tag{25}$$

Then the imaginary permittivity of the asphalt is approximated as $$\varepsilon''_r = \frac{\varepsilon'_{re}}{Q_{Asphalt}} \tag{26}$$

The resonant condition is perturbed from Equation (22) by the coupling structure. For instance, the coupled transmission line would have a minimum reflection coefficient and/or a maximum transmission coefficient when the impedance of the load is transferred to the complex conjugate at the input reference plane. Again, this is a function of the distance between the input and output launching structures and the propagation constant of the traversing wave. The launching structures could be a short section of microstrip line fed with an SMA connector and loop or gap coupled, or an antenna capable of launching microwave fields with a particular field orientation such as parallel to the surface of the waveguide/asphalt interface. Parallel fields are less susceptible to surface roughness (air gaps between the sensor and the material) than perpendicular Electric fields.

The following sample measurements included collecting the resonant frequency of the second harmonic, and the Q value of a microstrip resonant structure similar to FIG. 17. These measurements were in the range of 680 Mhz. The second harmonic will have a maximum electric field at both the ends of the resonator, as well as the center. These results were compared to the known density, which was resolved from a nuclear density gauge.

Figure 18:
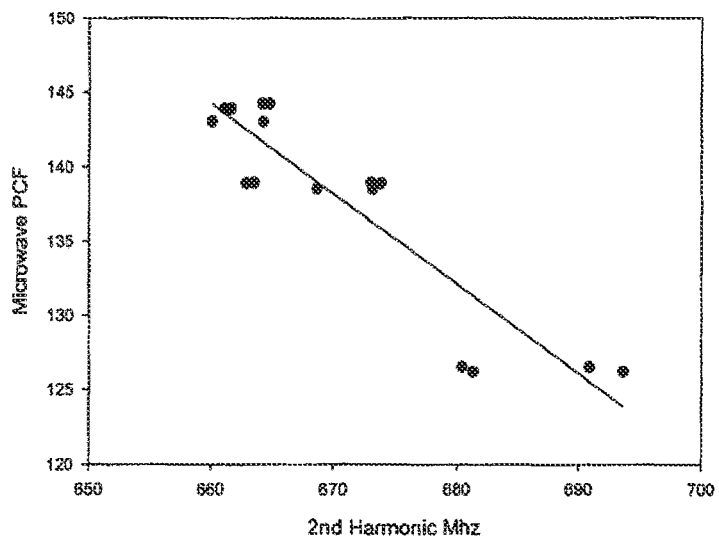
FIG. 18 is a plot of resonant frequency response to changes in density of samples tested by a microstrip microwave element for obtaining the density of a pavement material according to methods of one embodiment of the invention.
Figure 19A:
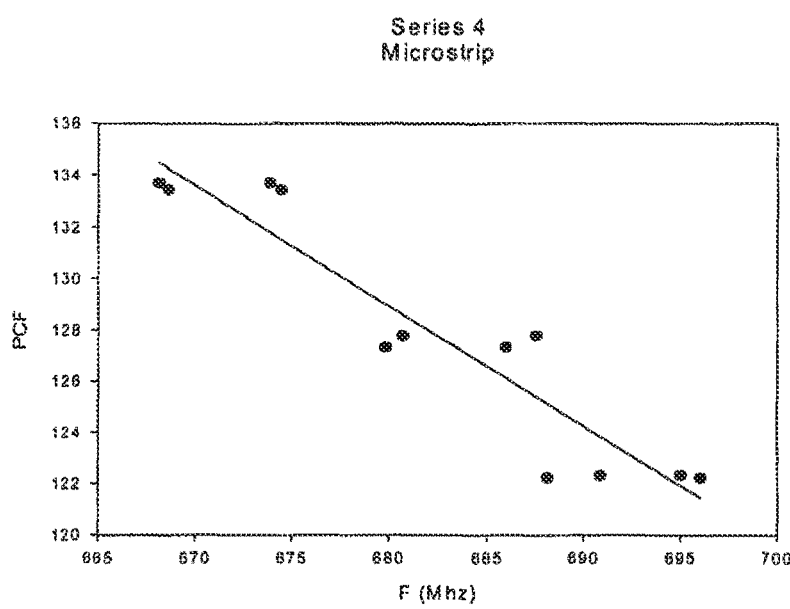
FIGS. 19(a) and (b) are plots of frequency and quality factor responses for samples of different densities tested by a microstrip microwave element for obtaining the density of a pave material according to methods of one embodiment of the invention.
Figure 19B:
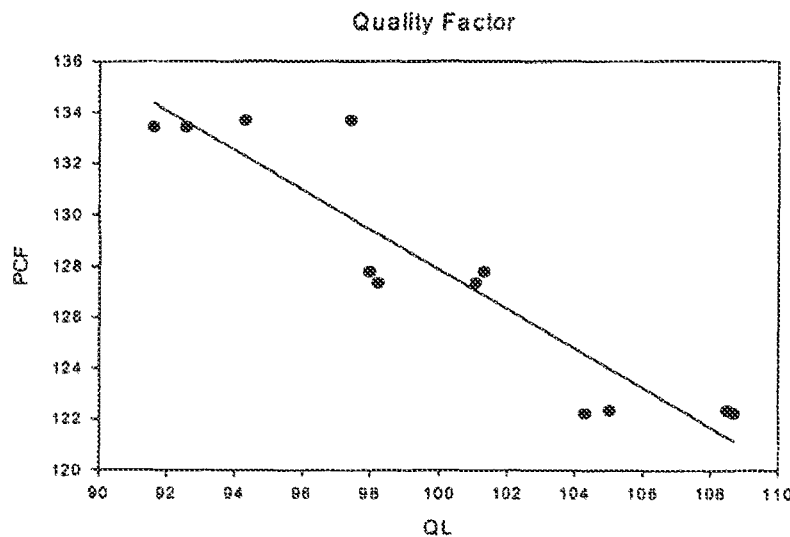

FIG. 18 shows the response of the resonant frequency to changes in density. Here, back calculation of dielectric constant is not required, and it is apparent frequency and density are therefore sufficient to calibrate the measurements. In FIGS. 19(a)-(b), both the real and imaginary frequencies were incorporated into the analysis yielding a loaded Q factor to changes in density, a two parameter curve fit. The curves of FIGS. 19(a)-(b) provided more consistent results. These two figures also illustrate that both the Q value and the resonant frequency behave in a linearly decreasing manner as the density increases for the microstrip device.

Surface Roughness Correction

While it is preferable that the surface of the asphalt sample be smooth or have a known roughness such samples are not practicable in the field or in the laboratory. Accordingly, it is desirable to include a roughness correction in conjunction with either or both of the embodiments of a density gauge described above. One embodiment of a roughness gauge is an electromagnetic system having two permittivity sensors. One sensor reads shallow (~0.25") depths below the surface, and a second sensor reads deeper (>2"), but also includes the shallow layer in its measurement volume. The sensor is electromagnetic, and uses the permittivity of the material to calculate the roughness. In one embodiment, the shallow sensor ran at 50 MHz and was a fringing field capacitance sensor such as disclosed in U.S. Pat. No. 6,803,771, incorporated herein by reference, while the deeper sensor was a microwave traveling wave type resonator, such as illustrated in FIG. 17. If the mix is constant over the two-inch depth, then it is reasonable to expect that the surface texture will affect the shallow sensor more than the deep sensor.

Figure 20:
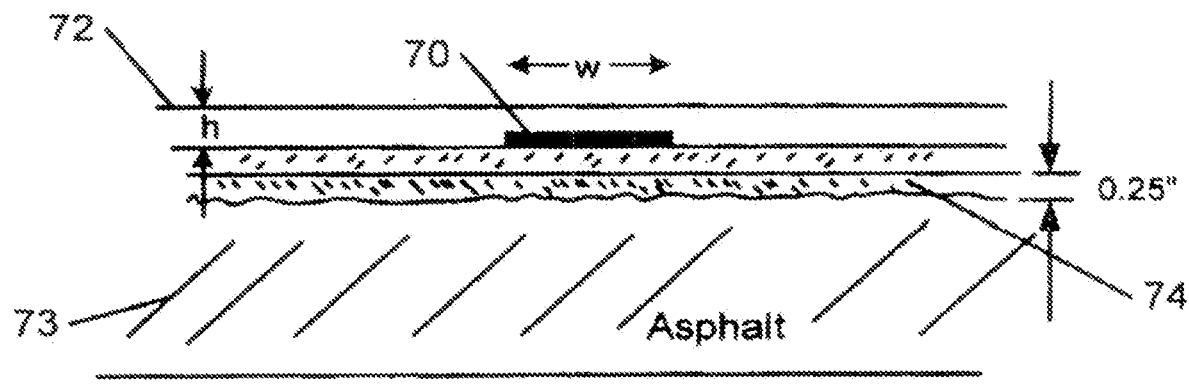
FIG. 20 is a microstrip microwave element disposed over a pavement material for obtaining the density of the pavement material according to methods of one embodiment of the invention.

Since it is extremely difficult to obtain perfect asphalt cores or slabs, a finite element simulation model validates the measurements differences. One embodiment is shown in FIG. 20 wherein the microwave device is a covered microstrip line 70 on a substrate 72 of thickness h place on asphalt 76 having a roughness 74. By solving for the propagation constant of the strip, the effective permittivity of the entire structure is determined. Resonant frequencies can then be found using the actual device dimensions.

This microstrip resonator 70 is 0.304 m long, 9.92 mm wide with gap coupling. A 1/32" thick epoxy FR-4 cover is glued directly on the strip as shown in FIG. 20. It was determined using the HP dielectric probe that this cover had $\epsilon$=4.0. The substrate 72 was thick and is Polyflon Norclad, $\epsilon$=2.55. In the simulations, the rough layer 74 was held at 0.25 inches deep, but the dielectric constant of this layer was adjusted from equal the underlying asphalt 76, to 50% less the asphalt value. Note that the rough layer has a permittivity that is equal to or less than the asphalt, because of the surface voids represented with the jagged line at the asphalt interface in FIG. 19.

Five sets of simulations were run at 600 MHz with different asphalt permittivities. These were $\epsilon$=3.0, 4.4, 6.17, and 7.11. These are all values of materials that are available in the lab. For each set of simulations, the asphalt dielectric constant was held constant, while the rough layer permittivity was changed. For each simulation, the rough layer was adjusted to correspond to a percent of the asphalt 6, mainly 100%, 90%, 80%, 60%, and 50%, except for the asphalt $\epsilon$=6.17, where 68% was used. The 68% was chosen so that the rough layer simulation would have a permittivity corresponding to FR-4 for laboratory verification.

The effective dielectric constant, $\epsilon_{re}$, of the (combined) substrate, cover, roughness layer, and asphalt was determined. The simulations were calibrated to remove the effects of the substrate by simulating the resonator on the known materials and obtaining the resonant frequency and Q value. A calibration curve and equation of the resonant frequency vs. the external material properties can be determined. Hence, absolute permittivities of any flat sample can now be obtained. From the model, the following results were obtained.

TABLE 5

| Asphalt $\epsilon$ = 7.11 Roughness Layer 1/4 in. Thick | | |
|---|---|---|
| Asphalt = 7.11 | $\epsilon_{re}$ of structure | Composite Permittivity |
| Rough = 7.11 | 3.43 | 7.112 |
| Rough = 6.4 | 3.35 | 6.661 |
| Rough = 5.7 | 3.27 | 6.209 |
| Rough = 4.27 | 3.08 | 5.137 |
| Rough = 3.55 | 2.97 | 4.517 |
| Rough = 7.725* $\epsilon_{re}$ - 19.46 | | |

| Asphalt $\epsilon$ = 6.17 | | |
|---|---|---|
| Asphalt = 6.17 | $\epsilon_{re}$ | Composite Permittivity |
| Rough = 6.17 | 3.26 | 6.153 |
| Rough = 5.55 | 3.19 | 5.758 |
| Rough = 4.94 | 3.12 | 5.363 |
| Rough = 4.2 | 3.03 | 4.855 |
| Rough = 3.1 | 2.87 | 3.952 |
| Rough = 7.875* $\epsilon_{re}$ - 19.57 | | |

| Asphalt $\epsilon$ = 4.4 | | |
|---|---|---|
| Asphalt $\epsilon$ = 4.4 | $\epsilon_{re}$ | Composite Permittivity |
| Rough = 4.41 | 2.95 | 4.404 |
| Rough = 3.96 | 2.90 | 4.122 |
| Rough = 3.52 | 2.84 | 3.783 |
| Rough = 2.64 | 2.72 | 3.106 |
| Rough = 2.2 | 2.66 | 2.768 |
| Rough = 7.50 $\epsilon_{re}$ - 17.76 | | |

| Asphalt $\epsilon$ = 3.0 | | |
|---|---|---|
| Asphalt $\epsilon$ = 3.0 | $\epsilon_{re}$ | Composite Permittivity |
| Rough = 3.0 | 2.7 | 2.993 |
| Rough = 2.7 | 2.66 | 2.768 |
| Rough = 2.4 | 2.62 | 2.542 |
| Rough = 1.8 | 2.54 | 2.091 |
| Rough = 1.5 | 2.49 | 1.808 |
| Rough = 7.22 $\epsilon_{re}$ - 16.49 | | |

Figure 21:
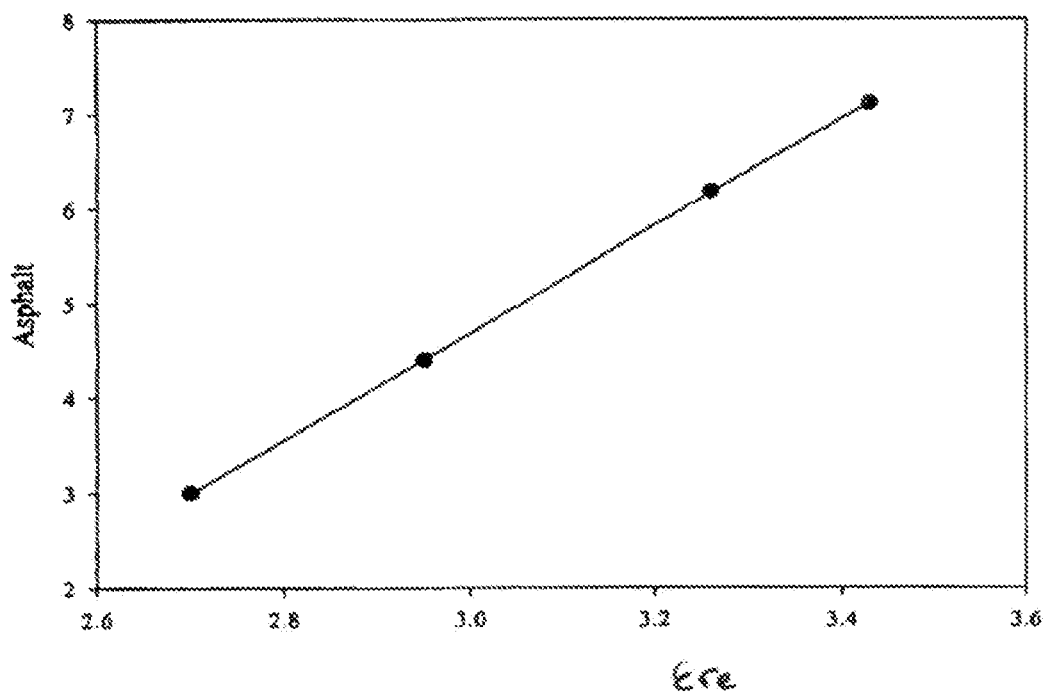
FIG. 21 is a plot of permittivity measurement of a deep layer of a pavement material to obtain a surface roughness correction according to embodiments and methods of the present invention.

Note that the first assignment to the rough layer is the value of the asphalt (2$^{nd}$ row of each table). With both layers assigned the same permittivity, the simulated calibration of a homogeneous smooth sample is accomplished by plotting the $\epsilon_{re}$ vs. the assigned external material property. Combining with the data of Table 1, we obtain the composite permittivity, $$\epsilon_{external} = 5.642 * \epsilon_{re} - 12.24. \quad (27)$$

where "external" represents the permittivity of the material excluding the microstrip substrate and cover. This equation is shown in FIG. 21 and represents the data of row 2 in the table for each $\epsilon_r$=7.11, 6.17, 4.4, 3.0. Note that FIG. 21 relates only to the perfectly smooth and homogenous surface. In other words, the asphalt layer and the rough layer have been assigned the same value. As the surface becomes textured, the permittivity of the rough layer will decrease. This will decrease the effective permittivity of the entire structure, even if the asphalt layer does not change. Equation (27) is still used to find this composite $\epsilon_r$. For the two-sensor system, the shallow sensor will have a larger reduction in permittivity than the deep sensor. It is this principle upon which the correction is based. The surface roughness correction should allow for the shallow layer permittivity to decrease, yet still obtain a good estimate of the permittivity of the deeper layer.

It is noteworthy that different permittivity combinations of asphalt and roughness can lead to the same effective or composite dielectric constant. If the asphalt $\epsilon_r=7.11$ and the surface is $\epsilon_r=4.27$ then table 1 shows $\epsilon_{external}=5.137$ as measured by the deep sensor. However, if the asphalt $\epsilon_r=6.14$ and it is relatively smooth pavement has a surface value of $\epsilon_r=4.68$, then the $\epsilon_{external}$ is also 5.137; according to table 1. A lower valued asphalt with a smoother surface could result in a higher effective permittivity than the higher valued asphalt with the rougher surface. Therefore, in one method a ratio of the shallow sensor/deep sensor result may used for correction. This way, for smooth surfaces, the ratio will be 1 and no correction is obtained. However, for a rougher surface, the ratio will be less than 1, but greater than zero, and a larger correction is obtained. For instance, in the example above, the ratios are 4.27/5.137=0.83, and 4.68/5.137=0.91. The second example with a factor of 0.91 is smoother than the 0.83 situation, and the correction will be much less.

In the finite element simulations, the results $\epsilon_{re}$ were converted to the external or "Top" values using Equation (27) of FIG. 21. To obtain a "first guess" of the deep layer dielectric constant. One possible correction for the actual permittivity could be where $$\epsilon_2=(\epsilon_X-\epsilon_1)*e^{(K*h1/w)}+\epsilon_1 \quad (28)$$

where $$K=(w/h_1)*In(2/(1+1/x)) \quad x=\sqrt{(1+12h/w)}, \quad (29)$$

w is the strip width 3/8", $h_1=1/4$" is the thickness of the rough layer, and $\epsilon_x$, $\epsilon_1$, and $\epsilon_2$ are the independent permittivities of the external layer, rough layer and deep layer respectively. Notice that the external layer .epsilon..sub.x is the composite response of both the rough and deep layer, as "measured" by the deep sensor. In Equation (28), as $h_1$ becomes small, $\epsilon_2=\epsilon_x$.

Figure 22:
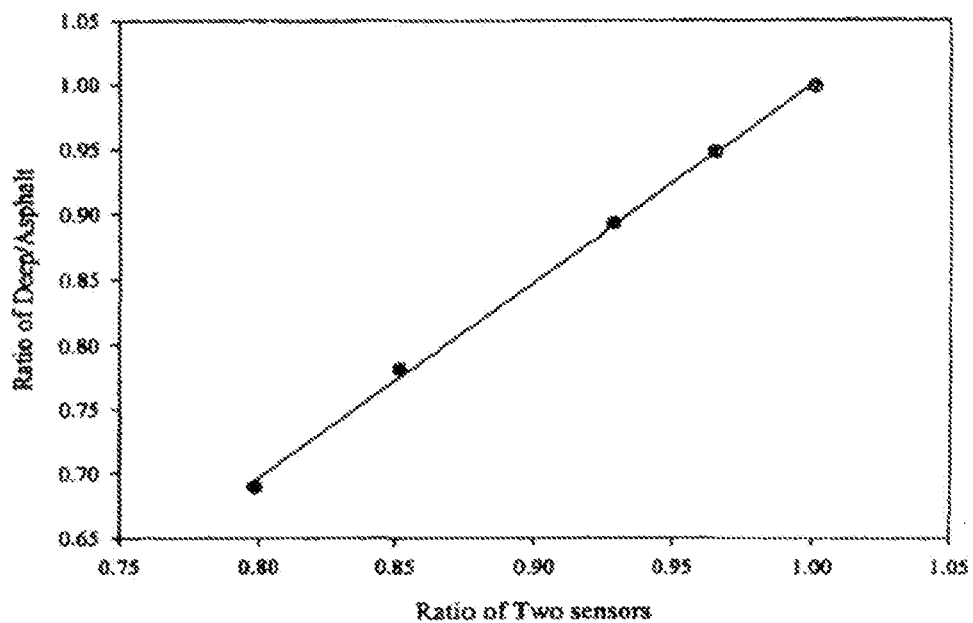
FIG. 22 is a plot of ratios of shallow and deep measurements of a pavement material to obtain a surface roughness correction according to embodiments and methods of the present invention.

Relationships between the external dielectric constant $\epsilon_x$ and the deep layer permittivity were also considered. A guess of $\epsilon_2$ is found using Equation (28). Taking a known permittivity value for the asphalt deep layer, and the deep layer "first guess," Equation (28), experimental results for the deep (D) and shallow (S) sensors can be compared to the ratio of the first guess ($\epsilon_2$) and known asphalt values ($\epsilon_{known}$). The finite element analysis calculated composite permittivities were used to obtain the values for the deep and shallow sensors. The experimental results indicate that the ratio of the measured shallow and deep sensors is related to the ratio of the deep layer and the composite layer. The experimental relationship is linear as shown in FIG. 22, where in this example the slope is 1.5187 and the intercept is 0.5184.

For example, suppose that the shallow sensor measured 5.55 and the deep sensor obtained the composite external dielectric constant of 5.75. Using slope and intercept from "first guess" of Equation 28, then the value of the asphalt layer would be (see the 6.17 asphalt layer in Table 1)

(5.55/5.75)*1.5187−0.5184=0.9454 Asphalt=5.86/0.9454=6.20.

Alternatively, it may not be necessary to use the "first guess," and only consider the measured values of deep and shallow sensors as compared to the known value. Therefore, the linear relationship between the ratio of the deep sensor $\epsilon_x$, and known deep permittivity can be plotted versus shallow sensor and deep sensor ratio values, resulting in a slope of 1.828 and an intercept of 0.8316.

Another roughness correction approach is to use actual core measurements to calculate the ratios of the known bulk permittivity ($\epsilon_{known}$) vs. the deep and shallow sensor ratios. For example, since there are two unknowns in the linear equation of FIG. 22, measurements on a smooth side and a rough side of the same core could be used for the roughness solution. One experimental core a very smooth cleaved side, the "X" side, and a normal rough side, the "O" side. In this example, the bulk permittivity ($\epsilon_{known}$) was measured in the microwave cavity and was found to be 5.75. This bulk number was assumed to be the permittivity just under the surface. Using the (D) deep microwave sensor and the (S) shallow UHF sensor the following dielectric constants were obtained, in Table 5.

TABLE 5

| Sensor | "X" = Smooth | "O" = Rough |
|---|---|---|
| Deep | 5.7 | 5.15 |
| Shallow | 5.6 | 4.24 |
| S/D | 5.6/5.7 | 4.24/5.15 |
| D/($\epsilon_{known}$) | 5.7/5.75 | 5.15/5.75 |

From this sample, two equations can be determined such that this sample yields lines "X" 5.9913=0.9820*m+b "O" 0.8956=0.8233*m+b.

Solving these simultaneously leads to $$D/Z=S/D*0.6027+0.4 \quad (30)$$

Therefore, by measuring the material with a deep and a shallow sensor, the composite permittivity found with the deep sensor, D, can be separated into the two layers, S and the unknown Z, as shown in Equation (30).

Another approach is to measure the two ends of an un-cleaved core, which typically have different textures, and to use a least squares method to calculate the average slope and intercept of Equation (30). Instead of using one core with one artificial smooth face and a normal face, a more realistic approach may be to measure many field mixes made into cores. In this method, it is assumed that the core is homogeneous, and that the same permittivity should be attained on each face of the sample. First the two sides are labeled as "X" and "O" sides. Then each sample is placed in a resonant closed cavity and the frequency and bandwidth shifts are recorded. A finite element analysis is run on the cavity and core dimensions, and the real part of the permittivity is found. With this method, the bulk permittivity ($\epsilon_{known}$) is the final result. Next, both the deep sensor (D) and the shallow sensor (S) are used to measure the permittivity of the "X" side and the "O" side of the puck. It is assumed that any differences in these two sides are due to the different texture or surface properties of the puck on each face. Once a good statistical population of cores is measured, a table of S/D, D/($\epsilon_{known}$) is formed for each sample on each side "X" and "O".

Figure 23:
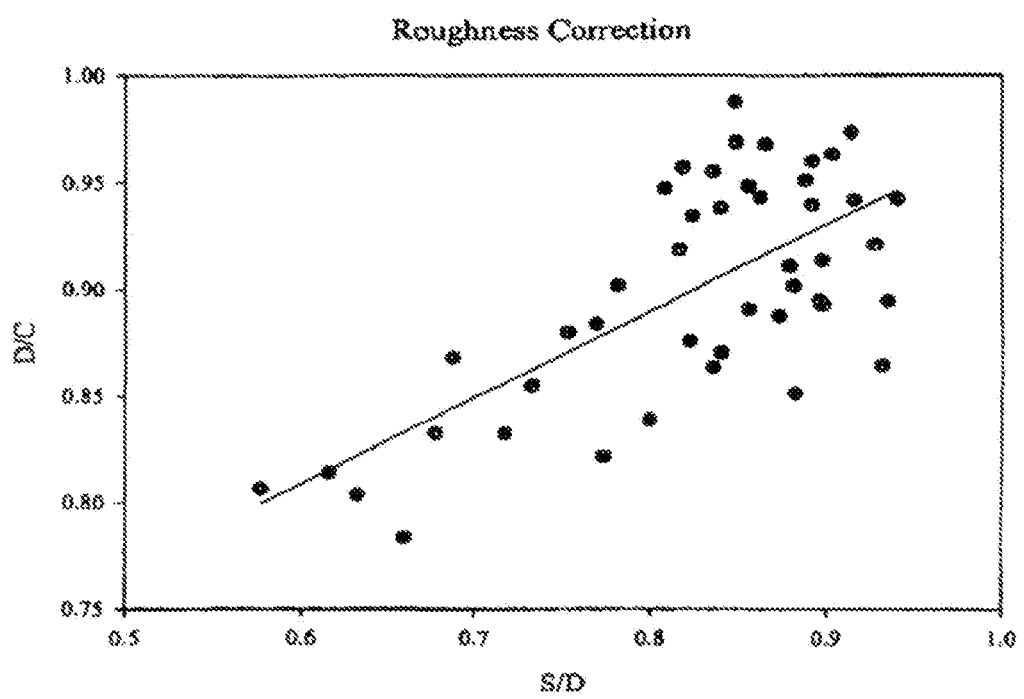
FIG. 23 is a plot of ratios of shallow measurements and deep measurement of a pavement material sample to obtain a surface roughness correction according to embodiments and methods of the present invention.

For example, each face is measured with the shallow sensor (S-200 @ 50 MHz) and the deep sensor (BS @ 600 MHz). The ratios S/D for both faces (X, O) are then plotted against the ratios D/C for each core in hopes that a correlation exists between these results, illustrated in FIG. 23.

The regression analysis indicates that $$D/(\epsilon_{known})=0.405*S/D+0.566 \quad (31)$$

With an r² of 0.482, the correlation coefficient may be improved with sensors that have less orientational properties and a better defined depth dependency, as the regression may indicate that the shallow sensor reads deeper than expected.

Accordingly, the two-layers can be simulated using finite elements to obtain equations that describe the calculation of the deep layer dielectric from the shallow and deep measurements. These equations would then be implemented and the coefficients adjusted for a calibration. Likewise, calibration may be empirical by placing the plates on known dielectric materials. In another modification of the surface roughness correction meter, the cavity measurements can be used to obtain the loss properties of the asphalt field or laboratory sample. The loss can be converted to conductivity, and a skin depth or depth of penetration can be calculated. It is well known that this depth is a function of frequency. Hence, by proper selection of frequency, an automatically depth dependent measurement can be obtained. In a slightly different embodiment, for surface waves, as the frequency increases, the surface waves excited by the sensors will penetrate less. This is due to both the losses due to the conductance, and the boundary solution to Maxwell's Equations for TE or TM type surface waves as known by those familiar in the art.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of operating a portable gauge for obtaining a material property of a pavement material from an electromagnetic field, the method comprising:
generating, using an electromagnetic field source, the electromagnetic field at a frequency of a first mode about the pavement material;
determining, using a multi-depth sensor, a frequency response of the pavement material in the electromagnetic field by performing a multi-depth permittivity measurement that includes:
measuring, using a first sensor, a first measured permittivity response of a first sample volume corresponding to at least a portion of a shallow surface layer of the material; and
measuring, using a second sensor, a second measured permittivity response of a second sample volume corresponding to at least a portion of a deep bulk layer of the material; and
correlating, using an analyzer, the frequency response to a material property of the pavement material, wherein correlating the frequency response to the material property includes:
obtaining a calibration data set for the first and second sensors based on a relationship of a predetermined calibration of the first and second sensors to a plurality of material permittivity responses; and
determining the property of a pavement material based on the first and second permittivity responses and the calibration data.

2. The method of claim 1, wherein the pavement material is a heterogeneous material and the determined property corrects for the surface roughness of the heterogeneous material.

3. The method of claim 1, further comprising:
obtaining a measurement relating to a physical property of a verified sample of a heterogeneous material;
measuring an impedance parameter of the verified sample of the heterogeneous material at one or more frequencies;
measuring an impedance parameter of a field sample of the heterogeneous material at one or more frequencies, wherein the impedance parameter includes at least one of impedance, admittance, resistance, capacitance, energy loss, phase velocity, phase shift, scattering parameters, reflection, transmission, VSWR, and combinations thereof; and
determining a relative density of the field sample to the verified sample based on the measured impedances.

4. The method of claim 3, wherein the physical property includes at least one of density, moisture, modulus, and texture of a construction material.

5. The method of claim 3, wherein obtaining measurements relating to a physical property of the verified sample includes placing the gauge on the surface of one or more compacted cylindrical heterogeneous material samples of known properties.

6. The method of claim 3, wherein obtaining measurements relating to a physical property of the verified sample includes performing the measurements using a fringing field capacitive sensor of a laboratory device separate from the portable gauge and mapping the measurements from the laboratory device to the portable gauge.

7. The method of claim 3, further comprising offsetting the gauge based on the density and the slope of at least one of: the density versus the impedance, density versus an impedance parameter, and the density versus the permittivity of the material.

8. The method of claim 3, wherein obtaining a measurement relating to a physical property of a verified sample of a heterogeneous material includes placing the gauge on a calibration material of determined properties including at least one of: permittivity, density, moisture, roughness.

9. The method of claim 3, further comprising measuring an impedance parameter for multiple field samples or sites in-situ of increasing density and calibrating the gauge in the field based on the measurements.

10. A portable gauge for obtaining a material property of a pavement material from an electromagnetic field, the gauge comprising:
an electromagnetic field source configured to generate the electromagnetic field at a frequency of a first mode about the pavement material;
a multi-depth sensor configured to determine a frequency response of the pavement material in the electromagnetic field by performing a multi-depth permittivity measurement, the multi-depth sensor comprising:

a first sensor configured to measure a first measured permittivity response of a first sample volume corresponding to at least a portion of a shallow surface layer of the material; and a second sensor configured to measure a second measured permittivity response of a second sample volume corresponding to at least a portion of a deep bulk layer of the material; and an analyzer configured to correlate the frequency response to a material property of the pavement material by:

obtaining a calibration data set for the first and second sensors based on a relationship of a predetermined calibration of the first and second sensors to a plurality of material permittivity responses; and determining the corrected pavement material property based on the calibrated first and second sensor responses.

11. The calibration of claim 10, wherein the relationship is at least one of: a data set, table, curve, simulation results and an equation relating at least one sensor permittivity response to materials representing the pavement material.

12. The portable gauge of claim 10, wherein the physical property of the heterogeneous material determined by the gauge includes at least one of: density, moisture, modulus, and texture of a construction material.

13. The portable gauge of claim 10, wherein the analyzer corrects a measured physical property of the second sensor based on the permittivity response of the first sensor, where the permittivity response of the first sensor is reduced by air voids related to the surface of the shallow surface layer of the pavement material and the first sensor.

14. The portable gauge of claim 13, wherein the corrected measurement of the second sensor is at least one: of a bulk density of an asphalt layer, bulk modulus, bulk moisture content, and surface texture of the pavement material.

15. The portable gauge of claim 10, wherein the first sensor depth is up to about 5-25 mm.

16. The portable gauge of claim 15, wherein the second sensor is configured to measure a portion of the deep bulk layer at a depth greater than the first sensor depth.

17. The portable gauge of claim 10, wherein the multi-depth sensor operates in the frequency domain from 0 to 50 MHz or a comparable bandwidth in the time domain.

18. The portable gauge of claim 10, wherein the multi-depth sensor operates up to the GHz range in the frequency domain or a comparable bandwidth in the time domain.

19. The portable gauge of claim 10, wherein the analyzer performs surface roughness correction based on a relationship of the first measured permittivity response corresponding to the shallow surface layer and the second measured permittivity response corresponding to the deep bulk layer.

20. The portable gauge of claim 18, wherein the measurement response includes at least one of: impedance, impedance parameters, admittance, energy loss, phase shift, scattering parameters, reflection, transmission, VSWR, phase velocity, and combinations thereof.

21. The portable gauge of claim 10, wherein the multi-depth sensor includes at least one of a planar capacitive sensor and a fringing field capacitive sensor.

22. The portable gauge of claim 10, wherein calibrating the first and second sensors to a plurality of pavement material permittivities includes placing the first and second sensors on a calibration material of known, relative, determined, or defined properties including at least one of: permittivity, density, moisture, roughness, and degree of roughness.

23. The portable gauge of claim 10, wherein calibrating the first and second sensors to at least one of a density, moisture content, modulus, and texture based on a plurality of pavement material permittivities includes obtaining calibration curves pertaining to at least one of the first and second sample volumes.

24. The portable gauge of claim 10, wherein the heterogeneous material includes at least one of: a pavement material, an asphalt material, and a soil construction material.

* * * * *